US005837854A

United States Patent [19]
Mulder

[11] Patent Number: 5,837,854
[45] Date of Patent: Nov. 17, 1998

[54] OLIGONUCLEOTIDES WITH ANTI-EPSTEIN-BARR VIRUS ACTIVITY

[75] Inventor: Carel Mulder, Worcester, Mass.

[73] Assignee: University of Massachusetts, Boston, Mass.

[21] Appl. No.: 628,422

[22] Filed: Apr. 5, 1996

[51] Int. Cl.$^6$ .......................... C07H 21/00; A61K 31/70; C12N 5/10
[52] U.S. Cl. .................. 536/24.5; 435/238; 435/375; 514/44
[58] Field of Search ................... 435/6, 240.1, 240.2, 435/238, 325, 375; 514/44; 536/23.1, 24.3, 24.5; 935/33

[56] References Cited

U.S. PATENT DOCUMENTS

| | | | |
|---|---|---|---|
| 5,194,428 | 3/1993 | Agarawal et al. | 514/44 |
| 5,242,906 | 9/1993 | Pagano et al. | 514/44 |
| 5,550,047 | 8/1996 | Mulder | 435/238 |
| 5,585,479 | 12/1996 | Hoke et al. | 536/24.5 |

FOREIGN PATENT DOCUMENTS

| | | |
|---|---|---|
| WO 91/12811 | 9/1991 | WIPO . |
| WO 92/04903 | 4/1992 | WIPO . |
| WO 93/07882 | 4/1993 | WIPO . |
| WO 93/11267 | 6/1993 | WIPO . |
| WO 94/19945 | 9/1994 | WIPO . |

OTHER PUBLICATIONS

Crystal "Transfer of genes to humans:Early lessons and obstacles to success" Science 270: 404–410, Oct. 1995.

Gewirtz et al. "Facilitating oligonucleotide delivery: Helping antisnese deliver on its promise" Proc. Natl. Acad. Sci. USA 93: 3161–3163, Apr. 1996.

Gura "Antisense for growing pains" Science 270: 575–577, Oct. 1995.

Stull et al. Antigene, ribozyme and aptamer nucleic acid drugs: Progress and prospects Pharm Res. 12: 465–483, Apr. 1995.

"Report and Recommendations of the Panel to Assess the NIH Investment in Research on Gene Therapy" Orkin and Motulsky, co–chairs. National Institutes of Health, Dec. 1997.

Agrawal et al., "Oligodeoxynucleoside Phosphoramidates and Phosphorothioates as Inhibitors of Human Immunodeficiency Virus", Proc. Natl. Acad. Sci. 85:7079–7083, 1988.

Baer et al., "DNA Sequence and Expression of the B95–8 Epstein–Barr Virus Genome", Nature 310:207–211, 1984.

Biggin et al., "Epstein–Barr Virus Gene Expression in P3HR1–Superinfected Raji Cells", J. Virology 61;3120, 1987.

Cheung et al., "Unexpected Patterns of Epstein–Barr Virus Gene Expression During Early Stages of B Cell Transformation", International Immunology 5:707–716, 1993.

Chevallier–Greco et al., "Both Epstein–Barr Virus (EBV)–encoded Trans-acting Factors EB1 and EB2, Are Required to Activate Transcription From an EBV Early Promoter", The EMBO Journal 5:3243–4249, 1986.

Daibata et al., "Antisense Oligodeoxynucleotides Against the BZLF1 Transcript Inhibit Induction of Productive Epstein–Barr Virus Replication", Antiviral Research 29:243–260, 1996.

Kevn, E. R., (1990) In: Antiviral Agents and Viral Diseases of Man, GJ Galass et al eds. pp. 94–95.

Pagano et al., "Epstein–Barr Viral Latency and Cell Immoratalization as Targets for Antisense Oligomers", Annals of The New York Academy of Sciences 660:107–116, 1992.

Roth et al., "Epstein–Barr Viral Nuclear Antigen 1 Antisense Oligodeoxynucleotide Inhibits Proliferation of Epstein–Barr Virus–Immortalized B Cells", Blood 84:582–587, 1994.

Tsubota et al., "Inhibited LMP Expression of EBV–Immortalized Lymphoblastoid Cells By Antisense Oligonucleotides", Investigative Ophthalmology & Visual Science 36:s992, Abstract 4592–573, 1995.

*Primary Examiner*—George C. Elliott
*Assistant Examiner*—Thomas G. Larson
*Attorney, Agent, or Firm*—Fish & Richardson P.C.

[57] ABSTRACT

Oligonucleotides that inhibit Epstein-Barr virus functions, pharmaceutical compositions containing such oligonucleotides, and methods of using these compositions to treat Epstein-Barr virus-associated diseases.

21 Claims, 6 Drawing Sheets

SEQUENCE LISTING ( 1 ) GENERAL INFORMATION:

( i i i ) NUMBER OF SEQUENCES: 63

( 2 ) INFORMATION FOR SEQ ID NO:1:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

TTTGGGTCCA TCATCTTCAG CAAAG    25

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:2:

CATCATCTTC AGCAAAGATA        20

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:3:

TCAGAAGTCG AGTTTGGGTC        20

( 2 ) INFORMATION FOR SEQ ID NO:4:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:4:

TTTGGGTC        8

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:5:

TTTGGGTCTC TCTTTGGGTC        20

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:6:

TTTGGGTCNN NNNNNNNNNN        20

( 2 ) INFORMATION FOR SEQ ID NO:7:

( i ) SEQUENCE CHARACTERISTICS:

(A) LENGTH: 18 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:7:

AAATTTTACA TCTTCAGA  18

(2) INFORMATION FOR SEQ ID NO:8:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:8:

GGGTCAGGTG TAAATTTTAC ATCTTCAGAA GTCGAGTTTG  40

(2) INFORMATION FOR SEQ ID NO:9:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:9:

CAGCACACAA GGCAAAGGAG  20

(2) INFORMATION FOR SEQ ID NO:10:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:10:

GCACCGGCCA CAGCACACAA GGCAAAGGAG CTTGCGATGG  40

(2) INFORMATION FOR SEQ ID NO:11:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:11:

CTCTGGCAGC ACCGGCCACA  20

(2) INFORMATION FOR SEQ ID NO:12:

(i) SEQUENCE CHARACTERISTICS:
(A) LENGTH: 40 base pairs
(B) TYPE: nucleic acid
(C) STRANDEDNESS: single
(D) TOPOLOGY: linear ( i i ) MOLECULE TYPE: DNA ( x i ) SEQUENCE DESCRIPTION: SEQ ID NO:12:

GTGGCAGAGG CTCTGGCAGC ACCGGCCACA GCACACAAGG     40

( 2 ) INFORMATION FOR SEQ ID NO:13:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:13:

CAGGCTGAGG GGCAGGAAAC     20

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:14:

CCCTCCTTAC CGATTCTGGC     20

( 2 ) INFORMATION FOR SEQ ID NO:15:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:15:

CTCCTTGATC CCCTCCTTAC CGATTCTGGC TGTAGTGGTT     40

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:16:

ATTCCTCCAG CTGCGAGCAA     20

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:17:

ATATACTGAC CTCACGGTAG     20

( 2 ) INFORMATION FOR SEQ ID NO:18:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:18:

CAGAAGCCAC CTGCGCACAA       20

( 2 ) INFORMATION FOR SEQ ID NO:19:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:19:

ATCCTTTTTA GGCCTCATGG CTAGTAGTAA       30

( 2 ) INFORMATION FOR SEQ ID NO:20:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:20:

ATCCTTTTTA GGCCTCATGG CTAGTAGTAA CAGAGGAAAT       40

( 2 ) INFORMATION FOR SEQ ID NO:21:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:21:

ATCCTTTTTA GGCCTCATGG TGCGTCTGTT TGTGTAGTGA       40

( 2 ) INFORMATION FOR SEQ ID NO:22:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:22:

ACAAATAAAT TTCTCTTACC TGCGTCTGTT TGTGTAGTGA       40

( 2 ) INFORMATION FOR SEQ ID NO:23:

( i ) SEQUENCE CHARACTERISTICS:

(A) LENGTH: 40 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:23:

ATGGTATTCT ACTTTAAAAA GGCCGGCTGA CATGGATTAC 40

(2) INFORMATION FOR SEQ ID NO:24:

(i) SEQUENCE CHARACTERISTICS:
(A) LENGTH: 40 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:24:

CTCAGAAAGT CTTCCAAGCC ATCCTTTTTA GGCCTCATGG 40

(2) INFORMATION FOR SEQ ID NO:25:

(i) SEQUENCE CHARACTERISTICS:
(A) LENGTH: 40 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:25:

ACAAATGTAA TTAAGAGGGA ACTAGAAAAC CAAAAAATTC 40

(2) INFORMATION FOR SEQ ID NO:26:

(i) SEQUENCE CHARACTERISTICS:
(A) LENGTH: 40 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:26:

TTTTAATGGC AAACAGTTAC CCGAGGTAAG CCGTTCCAGA 40

(2) INFORMATION FOR SEQ ID NO:27:

(i) SEQUENCE CHARACTERISTICS:
(A) LENGTH: 40 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:27:

AGAAGGTTGT TGGCATGTAC CTGCCCAACC ACAGGTTCAG 40

(2) INFORMATION FOR SEQ ID NO:28:

(i) SEQUENCE CHARACTERISTICS:
(A) LENGTH: 40 base pairs
(B) TYPE: nucleic acid
(C) STRANDEDNESS: single
(D) TOPOLOGY: linear ( i i ) MOLECULE TYPE: DNA ( x i ) SEQUENCE DESCRIPTION: SEQ ID NO:28:

AACTGAAATT CACAAATCAC CTGGCTAAGC CTGTGACTTA 40

( 2 ) INFORMATION FOR SEQ ID NO:29:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:29:

AGTCTCTGAG AAGGAACCAT CTTGTCTGTC TCTACGACGG 40

( 2 ) INFORMATION FOR SEQ ID NO:30:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:30:

CTGGCCGGTG TAGCTTCTTA CCTGCGGGAT CCTCGTTGGA 40

( 2 ) INFORMATION FOR SEQ ID NO:31:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:31:

AGTTCCAGAA TGTGGCTCTC TGCAGAGGGG AGACAAAAGG 40

( 2 ) INFORMATION FOR SEQ ID NO:32:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:32:

ACACAAGCAA GGCTGCCTCC ATTGTCTCGG CACCGATTTC 40

( 2 ) INFORMATION FOR SEQ ID NO:33:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:33:

ACCTGCTTAA ATGAAACCAT GGCAACCACT TCAAAGAGAG 40

( 2 ) INFORMATION FOR SEQ ID NO:34:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:34:

CTCTCAAGGT CGTGTTCCAT CCTCAGGGCA GTGTGTCAGG     40

( 2 ) INFORMATION FOR SEQ ID NO:35:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:35:

AAACAGTAGC GCCAAGAGGA GGAGAAGGAG AGCAAGGCCT     40

( 2 ) INFORMATION FOR SEQ ID NO:36:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:36:

GAGGACAAGG AGGGCTCCTC CAGTCCAGTC ACTCATAACG     40

( 2 ) INFORMATION FOR SEQ ID NO:37:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:37:

GCAAAGGGTG TAATACTTAC TCATCAGTAG GAGTATACAA     40

( 2 ) INFORMATION FOR SEQ ID NO:38:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:38:

AGCGATGAGC AGGAGGGTGA CTGGGGAAAG AGGAGAAAGT     40

( 2 ) INFORMATION FOR SEQ ID NO:39:

( i ) SEQUENCE CHARACTERISTICS:

(A) LENGTH: 40 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:39:

ATCTTACCAA GTAAGCACCC GAAGATGAAC AGCACAATTC           40

(2) INFORMATION FOR SEQ ID NO:40:

(i) SEQUENCE CHARACTERISTICS:
(A) LENGTH: 52 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:40:

CATCTCCAAT AAGTAGATCC AGATACCTAA GACTGCGTTG AAAAAGATG TT           52

(2) INFORMATION FOR SEQ ID NO:41:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:41:

AACTTTACAC CACGTCACAC GCCAGTGCTG GGTTACTGCG           40

(2) INFORMATION FOR SEQ ID NO:42:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:42:

ATTAGATGAT ATGTTTGTCC CCCATGTAAC GCAAGATAGA           40

(2) INFORMATION FOR SEQ ID NO:43:

(i) SEQUENCE CHARACTERISTICS:
(A) LENGTH: 40 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:43:

GGCAGGCATA CTGGATTCAT ACTAAGAAAG AGAACGGGCA           40

(2) INFORMATION FOR SEQ ID NO:44:

(i) SEQUENCE CHARACTERISTICS:
(A) LENGTH: 40 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:44:

AATGGTGCGT GTGTACTCAC AAGTGACAAC CGCAGTAA GC 40

(2) INFORMATION FOR SEQ ID NO:45:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:45:

ATGTTAGGCA AATTGCAAAG ACTGAGGAGA AAAGCAGAGG 40

(2) INFORMATION FOR SEQ ID NO:46:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:46:

CATAACAGAG GCACACTAAC CGTAAATGCC TTGTAGTCCG 40

(2) INFORMATION FOR SEQ ID NO:47:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:47:

GGAGCACAAG CATCACCAGA ACTGAAATAA AAGTAAAGTT 40

(2) INFORMATION FOR SEQ ID NO:48:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:48:

ATGTCACACG TGTGGCTTAC CTGCTGCCAA TGTTAAAAGG 40

(2) INFORMATION FOR SEQ ID NO:49:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (i i) MOLECULE TYPE: DNA (x i) SEQUENCE DESCRIPTION: SEQ ID NO:49:

TGACGCTAGC AGTGCCAGAG CTATAATCAG AGATGGCATG 40

( 2 ) INFORMATION FOR SEQ ID NO:50:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:50:

AAAGGAAGGG AAAACTTACC AAGTGTCCAT AGGAGCATGA 40

( 2 ) INFORMATION FOR SEQ ID NO:51:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:51:

AGAGCAAATC AGGAGAACCA CTGTAAAAGA GATGCCAAGT 40

( 2 ) INFORMATION FOR SEQ ID NO:52:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:52:

GTAACAAATA GATACTCACT GGGTATAAAT TCAGTGCTGC 40

( 2 ) INFORMATION FOR SEQ ID NO:53:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:53:

GTAATAACAT GCAGAACAAA TCTAAGGAAC AAAGCGTAAA 40

( 2 ) INFORMATION FOR SEQ ID NO:54:

( i ) SEQUENCE CHARACTERISTICS:
    ( A ) LENGTH: 40 base pairs
    ( B ) TYPE: nucleic acid
    ( C ) STRANDEDNESS: single
    ( D ) TOPOLOGY: linear ( i i ) MOLECULE TYPE: DNA ( x i ) SEQUENCE DESCRIPTION: SEQ ID NO:54:

CCTGTTGGTG TCACACTTAC CAATGAGGAA AATCAGGAAT 40

( 2 ) INFORMATION FOR SEQ ID NO:55:

( i ) SEQUENCE CHARACTERISTICS:

(A) LENGTH: 40 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:55:

TGACCCCAAA GAGGGCAAAG CCTACAAAAG CCAAACCCAT 40

(2) INFORMATION FOR SEQ ID NO:56:

(i) SEQUENCE CHARACTERISTICS:
(A) LENGTH: 40 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:56:

TAAAATTTAA TAATACTTAC CTTTATACAG TGTTGCGATA 40

(2) INFORMATION FOR SEQ ID NO:57:

(i) SEQUENCE CHARACTERISTICS:
(A) LENGTH: 40 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:57:

GCAGGCGATC TGGTGGGCAT TCTGCAAAAC ATATGGCATC 40

(2) INFORMATION FOR SEQ ID NO:58:

(i) SEQUENCE CHARACTERISTICS:
(A) LENGTH: 40 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:58:

GCACCATTTC TAGGGACCCC ATAGCTGCAG CAGCGACTGC 40

(2) INFORMATION FOR SEQ ID NO:59:

(i) SEQUENCE CHARACTERISTICS:
(A) LENGTH: 40 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:59:

CAGATAGATG GCACTCTTAC CTTCCTCTGC CCGCTTCTTC 40

(2) INFORMATION FOR SEQ ID NO:60:

(i) SEQUENCE CHARACTERISTICS:
(A) LENGTH: 40 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:60:

GGCAGGCATA CTGGATTCAT ACTGAACCCC CCTAAAGCAC 40

(2) INFORMATION FOR SEQ ID NO:61:

(i) SEQUENCE CHARACTERISTICS:
(A) LENGTH: 40 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:61:

ACCCCACAGC CTTGCCTCAC CTGAACCCCC CTAAAGCACG 40

(2) INFORMATION FOR SEQ ID NO:62:

(i) SEQUENCE CHARACTERISTICS:
(A) LENGTH: 25 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:62:

GAAACGACTT CTACTACCTG GGTTT 25

(2) INFORMATION FOR SEQ ID NO:63:

(i) SEQUENCE CHARACTERISTICS:
(A) LENGTH: 25 base pairs
(B) TYPE: nucleic acid
(C) STRANDEDNESS: single
(D) TOPOLOGY: linear (i i) MOLECULE TYPE: DNA (x i) SEQUENCE DESCRIPTION: SEQ ID NO:63:

CTTTGCTGAA GATGATGGAC CCAAA 25

OLIGONUCLEOTIDES WITH ANTI-EPSTEIN-BARR VIRUS ACTIVITY

BACKGROUND OF THE INVENTION

This invention relates to oligonucleotides, pharmaceutical compositions containing such oligonucleotides, and methods of using these compositions for the treatment of pathology associated with Epstein-Barr virus infection.

Epstein-Barr virus (EBV) is a ubiquitous human herpesvirus which infects the majority of the population and is associated with disease and neoplasia. A double-stranded DNA virus of 172 kb, EBV can infect lymphocytes and epithelial cells. Infection of B lymphocytes with EBV results in their activation and proliferation. In most individuals, primary EBV infection occurs during childhood and does not result in clinical manifestations. If primary infection is delayed until adolescence, infectious mononucleosis (IM), a self-limiting proliferation of EBV-infected B cells, can result.

Subsequent to primary infection, EBV-infected cells persist within the host for life. Low levels of infectious virus are produced by epithelial cells in most asymptomatic seropositive individuals. EBV-infected B cells are kept from proliferating out of control in vivo by a properly functioning immune system. In individuals who are immunosuppressed, however, EBV-infected cells can give rise to lymphoproliferative disorders leading to disease or neoplasia.

EBV infection is associated with a number of pathological conditions, such as X-linked lymphoproliferative syndrome (XLP), malignancies such as nasopharyngeal carcinoma (NPC), and many cases of Burkitt Lymphoma (BL) and Hodgkin's Disease (HD) (reviewed in Rickinson et al., Virology, Fields et al., eds., 3d ed. 1996, pp. 2397–2446, Lippincott-Raven, Philadelphia, Pa.). Further, immunosuppressed individuals, e.g., organ transplant recipients being treated with immunosuppressive drugs, can develop EBV-positive B cell lymphomas. Individuals infected with human immunodeficiency virus (HIV) can also develop EBV-positive B cell lymphomas, which are called AIDS-related lymphomas (ARLs). Oral hairy leukoplakia (OHL), which manifests itself as EBV-infected epithelial lesions on the tongue, has also been observed in AIDS patients.

Like other herpesviruses, EBV undergoes both latent and lytic phases (reviewed in Kieff, Virology, Fields et al., eds., 3d ed. 1996, pp. 2343–2396, Lippincott-Raven, Philadelphia, Pa.). Latent EBV infection is characterized by an absence of the production of infectious virus. EBV generally assumes the latent state upon primary infection of B lymphocytes. During latency, the virus is maintained in B cells as multiple copies of a circular episome.

To replicate and be maintained within latently infected cells, the EBV episome requires the presence of Epstein-Barr virus nuclear antigen 1 (EBNA-1), which is encoded by the viral gene BKRF1, and which interacts with the viral origin of replication, orip. Several other EBNA proteins are also expressed during latency, including EBNA-2, which is encoded by the BYRF1 gene and transactivates cellular and viral genes.

Several membrane proteins are also expressed during EBV latency including the Latent Membrane Protein (LMP) -1, which has been shown to be a transforming protein. Terminal Proteins 1 and 2 (TP-1 and TP-2 or LMP-2A and LMP-2B), which are involved in transmembrane signal transduction, are also expressed in latently infected cells.

To produce infectious EBV, latently infected cells must enter the viral lytic or productive phase. Lytic infection is characterized by the expression of many viral proteins, which are classified according to the stage at which they are produced. Immediate Early (IE) genes are the first genes to be expressed during the EBV lytic cycle. Expression of the protein encoded by the IE viral gene BZLF1 is necessary for the initiation of the lytic cycle of EBV. The BZLF1 gene product, also known as ZEBRA, EB-1, and Zta, has pleiotropic functions in the regulation of EBV infection. ZEBRA is a transactivator which autoregulates its own expression by binding to AP-1-like sites upstream of BZLF1 and increasing its transcription. ZEBRA also activates the expression of another IE gene, BRLF1, which encodes a transactivating protein. BZLF1 and BRLF1 are believed to act in concert to initiate further events in lytic infection, culminating in production and release of infectious EBV.

The protein products of the IE genes activate the Early genes. Early genes include BMRF1, which encodes the diffuse component of the EBV Early Antigen Complex (EA-D), and BMLF1 and BSLF2, which, like the gene products of BZLF1 and BRLF1, are transactivating proteins. Another Early gene is BHRF1. BHRF1 is homologous to the cellular gene bcl2, expression of which prevents apoptotic cell death. Other Early genes, such as BALF5, which encodes the EBV DNA polymerase, encode proteins involved in the replication of EBV DNA to be packaged into virions.

Once the Early genes are expressed, replication of lytic EBV can commence. Lytic EBV replication requires that the ZEBRA protein interact with the origin of EBV lytic replication, orilyt. EBV produced during the lytic phase and packaged into virions is linear.

Expression of the Early genes is followed by expression of the Late genes, which encode proteins involved in virion structure and assembly. Late gene products include gp350, the major virion glycoprotein of EBV, which is encoded by the BLLF1 gene, and gp42, another virion glycoprotein, which is encoded by the BZLF2 gene. The EBNA-1 and LMP-1 proteins, which are produced during the EBV latent cycle, continue to be expressed during the lytic phase of EBV.

In some EBV-associated diseases, such as most EBV-positive BLs, the virus apparently maintains itself in a latent state, although the latent EBV genome can be induced to enter the lytic cycle by various stimuli. In other diseases, e.g., OHL, EBV is generally in the lytic phase of the viral life cycle.

Other EBV-associated tumors undergo an abortive lytic cycle, in that they express the viral protein ZEBRA, which initiates the EBV lytic cycle, yet they do not progress fully through the lytic cycle to production and release of virions. See, e.g., Pagano, Cancer 74: 2397 (1994); Cochet et al, Virology 197: 358–365 (1993); Pallesen et al., J. Pathol. 165: 289–299 (1991). For example, AIDS-related lymphomas (ARLs) are proliferations of B lymphocytes which show many of the characteristics of latent EBV infection. However, while biopsy materials from ARLs show little or no expression of Late antigens such as viral capsid antigen (VCA), up to 60% of the cells express ZEBRA. Pallesen et al., J. Pathol. 165; 289–299 (1991). ZEBRA is also expressed in some NPCs and HDs, although neither of these tumors progresses fully through the EBV lytic cycle. Cochet et al., Virology 197: 358–365 (1993); Pallesen et al., Blood 78: 1162–1165 (1991). Expression of ZEBRA may contribute to the tumorigenicity of these infected cells. Among individuals with NPC, those who have a high antibody titer to ZEBRA have a poorer prognosis than those with a low anti-ZEBRA titer. Yip et al., *Cancer* 74: 2414–2424 (1994). ZEBRA has been shown to physically interact with the tumor suppressor gene p53, which normally acts as a regulator of cell growth, both in vivo and in vitro. Zhang et al., *Mol. Cell. Biol.* 14: 1929–1938. This association with ZEBRA inhibits p53 functions, and thus may be a major factor in EBV-associated oncogenicity.

Different approaches have been used to attempt to reduce pathology associated with EBV infection. For example, pyrophosphate analogs, thymidine kinase analogs, ribonucleoside reductase inhibitors, and nucleoside analogs, such as acyclovir, have been used to control diseases associated with EBV infection. None of these agents has been ideal in inhibiting EBV replication and associated pathology. In addition, these agents do not specifically inhibit EBV functions, and their use can result in inhibition of normal cellular processes, which in turn results in undesirable side effects. Antisense oligodeoxynucleotides have also been designed that are specific for the BHLF1 gene, which is associated with the EBV lytic cycle, and the gene encoding EBNA-1, which is associated with the EBV latent cycle. U.S. Pat. No. 5,242,906; Roth et al., *Blood* 84: 582–587 (1994); WO 93/11267.

SUMMARY OF THE INVENTION

The invention features antisense oligonucleotides that inhibit EBV functions such as replication and gene expression, pharmaceutical compositions containing such oligonucleotides, and methods of using these compositions to treat EBV-associated diseases. The oligonucleotides are delivered to a patient, e.g., a mammal such as a human, either as the antiviral oligonucleotides themselves, or by the administration of expression vectors that produce multiple copies of the antisense oligonucleotides intracellularly.

In some embodiments, the antisense oligonucleotides are specific for, i.e., complementary to, target sequences found in EBV genes that are generally associated with the viral latent cycle. These genes include BNLF1, which encodes LMP-1; BYRF1, which encodes EBNA-2; and the genes encoding TP1 (LMP-2A) and TP2 (LMP-2B).

In other embodiments, the antisense oligonucleotides are specific for target sequences found in EBV genes that are generally associated with the viral lytic cycle. These genes include BZLF1, which encodes the ZEBRA transactivating protein; BRLF1, BMLF1, and BSLF2, which also encode transactivating proteins; BHRF1, which encodes a protein which is homologous to bcl-2; and BLLF1 and BZLF2, which encode the EBV virion glycoproteins gp350 and gp42, respectively.

Sequences of the oligonucleotides, the genes to which they are targeted, and the location (position numbers) of these genes in the EBV genome are set forth in Table I. "Core regions" of eight nucleotides for each oligonucleotide are indicated by underlining. While the entire sequence of the oligonucleotides described in Table I can be synthesized and used, shorter oligonucleotides containing only a portion of the sequences shown in Table I also can be synthesized and used as described herein. However, such shorter oligonucleotides preferably contain the core region. The oligonucleotides are typically 12–40 nucleotides in length, are preferably 15–25 nucleotides in length, and can include the core region at either end or in the middle of the oligonucleotide. They can be deoxyribonucleotides, ribonucleotides, or a combination.

The oligonucleotides can also be "counterparts" of the sequences listed in Table I derived from other strains of EBV. The sequences described in Table I are based on the nucleotide sequence of the B95-8 or Akata EBV strains. There is known variation in the nucleotide sequences of different strains of EBV, and oligonucleotides specific for target regions within genes named in Table I, but located in the same genes in other strains of EBV, may vary somewhat in nucleotide sequence from the oligonucleotides listed in Table I. Thus, oligonucleotides specific for the same target regions as listed in Table I, but in other strains of EBV having varied nucleotide sequences, are referred to herein as "counterpart" oligonucleotides.

The antisense oligonucleotides also can be labelled and used as probes to determine if particular cells are infected with EBV.

As used herein, "modified oligonucleotide" means an oligonucleotide in which the deoxyribonucleic or ribonucleic acid structure has been altered in some way compared to the natural state of the nucleotides in the sequence. For example, the oligonucleotides can be modified to achieve greater stability such as by replacement of phosphodiester internucleoside linkages with phosphorothioate, methylphosphonate, alkylphosphonate, phosphorodithioate, alkylphosphonothioate, phosphoramidate, phosphate ester, carbamate, acetamidate, carboxymethyl ester, carbonate, or phosphate triester linkages. The oligonucleotides also can be modified with methylphosphonodiester linkages, with 3' deoxythymidine, as a phenylisourea derivative, or by linking other molecules such as aminoacridine or polylysine to the 3' end of the oligonucleotide, to block against exonuclease attack. Methods of making these modified oligonucleotides are well known in the art. See, e.g., *Anticancer Research* 10: 1169–1182 at 1171–1172 (1990).

Other modifications include (1) the addition of compounds such as diamines or cholesterol with varying numbers of carbon residues between the amino groups and terminal ribose, deoxyribose, and (2) phosphate modifications that cleave, or crosslink to the opposite chains or to associated enzymes or to other proteins that bind to the viral genome.

In other embodiments, the oligonucleotides have a modified base or a modified sugar, such as arabinose instead of ribose. Modified oligonucleotides include those with a sugar having a chemical group other than a hydroxyl attached at its 3' position, or a chemical group other than a phosphate attached at its 5' position. The oligonucleotides also can be capped with a nuclease resistance-conferring bulky substituent, or have a substitution in a nonbridging oxygen. Modifications can be in some or all of the nucleotides, as well as at either or both ends of the oligonucleotide or in its interior.

Another embodiment is an oligonucleotide formulated with a transfection reagent, e.g., lipofectin or one of its derivatives, which increases the efficiency of cellular uptake of the oligonucleotide, and/or reduces the amount of oligonucleotide necessary to produce a response.

The antisense oligonucleotides also can be formulated in a ribozyme structure. For example, structures can be designed in which EBV-specific oligonucleotides flank a ribozyme. The antisense oligonucleotides thus target the ribozyme to specific EBV sequences.

The invention further features a pharmaceutical composition including an antiviral oligonucleotide and a pharmaceutically acceptable carrier.

Specific cell types can be targeted by these pharmaceutical compositions by conjugating the oligonucleotides to monoclonal antibodies specific for cell surface receptors involved in receptor-mediated endocytosis. The oligonucleotides or their derivatives can also be administered in liposomes, microspheres, or other vehicles designed to increase cellular uptake. These vehicles can be made specific for certain cell types by incorporating antibodies directed against specific cell surface receptors.

In another aspect, the invention features a method of treating or inhibiting EBV functions such as replication or expression of viral proteins to treat a condition which is associated with EBV infection. The method includes the step of administering to a mammal a therapeutically effective amount of one or more antisense oligonucleotides, or of an expression vector that encodes these oligonucleotides intracellularly. Such an expression vector preferably includes transcription control sequences that facilitate expression of the oligonucleotide in EBV-infected cells, e.g., the oligonucleotide can be expressed from a plasmid containing the B cell-specific EBV origin of replication, orip, which includes B cell-specific enhancer sequences (Reisman et al., Mol. Cell. Biol. 6: 3838–3846 (1986)), and which functions only in the presence of the viral gene EBNA-1.

As used, herein, "pharmaceutical composition" means a composition for administration to a patient, e.g., a mammal, such as a dog, horse, cow, or human. A pharmaceutical composition can include any and all solvents, dispersion media, coatings, antibacterial and antifungal agents, isotonic and absorption delaying agents, and the like. Supplementary active ingredients can also be incorporated into the compositions. The use of such media and agents is well known in the art.

"Complementary," when referring to a nucleotide sequence, means that the nucleotide sequence has the capacity to precisely pair its purine and pyrimidine bases to those of another nucleotide strand, such that sequence of one strand determines the sequence of the other. On a individual nucleotide level, A is the complement of T, and C is the complement of G. For example, an "antisense" nucleotide sequence is complementary to a target nucleotide sequence in a gene.

Unless otherwise defined, all technical and scientific terms used herein have the same meaning as commonly understood by one of ordinary skill in the art. Although methods and materials similar or equivalent to those described herein can be used in the practice or testing of the invention, the preferred methods and materials are described below. All publications, patent applications, patents and other references mentioned herein are incorporated by reference. In addition, the materials, methods and examples are illustrative only and not intended to be limiting. In case of conflict, the present specification, including definitions, controls.

Other features and advantages of the invention will be apparent from the following detailed description, and from the claims.

DETAILED DESCRIPTION

Figure 1:
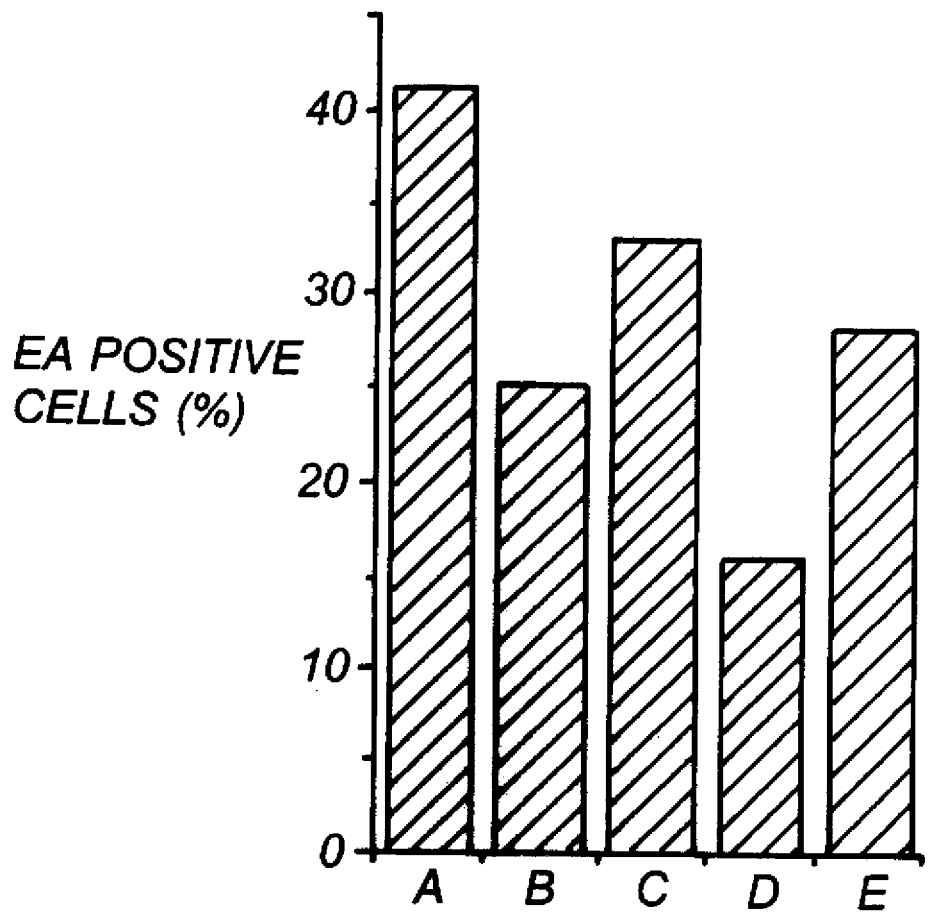
FIG. 1 is a graph showing the levels of EBV Early Antigen (EA-D) expression after induction of the EBV lytic cycle in Akata cells treated with: (A) medium alone; (B) phosphodiester-linked (PO) BZLF1 antisense oligonucleotides (SEQ ID NO:1); (C) PO control oligonucleotides; (D) phosphorothioate-linked (PS) BZLF1 antisense oligonucleotides (SEQ ID NO:1); and (E) PS control oligonucleotides.

The invention features antisense oligonucleotides that inhibit Epstein-Barr virus functions, such as gene expression and replication, pharmaceutical compositions containing these oligonucleotides, and methods of using these compositions to treat EBV-associated diseases. Oligonucleotides used to treat specific diseases are chosen on the basis of the EBV genes expressed in those diseases. For example, BZLF1 antisense oligonucleotides are administered to EBV-infected tumor cells that express BZLF1. These BZLF1 antisense oligonucleotides inhibit EBV gene expression and replication, and this inhibition is enhanced when combinations of different BZLF1 antisense oligonucleotides are used. BZLF1 antisense oligonucleotides also act synergistically with BRLF1 oligonucleotides to inhibit EBV functions. The use of transfection reagents reduces the amount of oligonucleotide necessary to obtain an effective response.

The ability of antisense oligonucleotides to inhibit EBV functions can be evaluated using in vitro and in vivo models.

Akata cells

Akata cells, described in Takada et al., J. Virol. 63: 445–449 (1989), were maintained in RPMI 1640 medium supplemented with penicillin (100 IU/ml), streptomycin (100 μg/ml), and 10% heat-inactivated fetal calf serum (FCS) at 37° C. in a humidified atmosphere of 5% $CO_2$ in air. The EBV lytic cycle was induced in these cells by treatment with 100 μg/ml of antibody to human IgG (Cappel, West Chester, Pa.) (Daibata et al., 1990).

P3HR-1 Cells

P3HR-1 cells, described by Hinuma et al., J. Virol. 1:1045–1051 (1967) were maintained in RPMI 1640 medium supplemented with penicillin (100 IU/ml), streptomycin (100 μg/ml), and 10% heat-inactivated FCS in a humidified atmosphere of 5% $CO_2$ in air. The cells were incubated at 33° C., since the production of EBV by P3HR-1 cells is higher upon incubation at 33° C. than at 37° C.

Oligonucleotides

Phosphodiester linked (PO) and phosphorothioate linked (PS) oligonucleotides were synthesized on an automated DNA synthesizer (Applied BioSystems Inc., Foster City, Calif.) according to the manufacturer's instructions. The oligonucleotides were purified by reverse-phase high performance liquid chromatography (HPLC), detritylated, ethanol precipitated, and analyzed by polyacrylamide gel electrophoresis (PAGE). BZLF1 oligonucleotides synthesized included a 25-mer oligonucleotide having the sequence 5'-TTT GGG TCC ATC ATC TTC AGC AAA G-3' (designated Z1; SEQ ID NO:1), which spans the translation initiation codons (AUG) of the BZLF1 mRNA. In addition, two BZLF1 antisense oligonucleotides that are adjacent to each other and which partially overlap with the Z1 sequence were also synthesized: the 20mer 5'-CAT CAT CTT CAG CAA AGA TA-3' (designated Z2, SEQ ID NO:2), and the 20mer 5'-TCA GAA GTC GAG TTT GGG TC-3' (designated Z3, SEQ ID NO:3). The Z2 oligonucleotide is complementary to a sequence from the 5' untranslated region of BZLF1 to the two AUGs present at the initiation of the open reading frame. Z3 is complementary to a BZLF1 sequence immediately downstream of the AUGS.

Other antisense oligonucleotides specific for EBV genes are listed in Table I. The antisense sequences that are specific for BZLF1, as well as the R1 oligonucleotide, which is specific for BRLF1, were designed to be complementary to portions of the sequence of the Akata BZLF1 gene. Packham et al., *Virology* 192: 541–550 (1993). Sequences for the other oligonucleotides were designed based on the sequence of the prototype B95-8 strain of EBV. Baer et al., *Nature* 310: 207–211 (1984). The EBV genome coordinates given in Table I refer to the nucleotide position numbers in the EBV genome to which the oligonucleotides are complementary. The EBV genome coordinates listed in Table I refer to nucleotide position numbers in the B95-8 genome, regardless of whether the sequence of the oligonucleotide was designed based on the B95-8 sequence or the Akata sequence. There is some sequence diversity among different strains of EBV, and some strains have sustained deletions and insertions within the EBV genome. Therefore, the particular region identified by the B95-8 coordinates may be in a different, but correlatable, location in another strain of EBV.

As indicated in Table I, some of the oligonucleotides are specific for regions containing splice sites, while others are specific for regions containing translation initiation (AUG) codons. Table I also indicates which of the oligonucleotides were designed using an RNase H assay. In this assay, RNAs are in vitro transcribed, end-labelled, and incubated with random oligonucleotides. RNAse H is then added to specifically cleave RNA-DNA hybrids. Those sites which are cleaved represent areas on the RNA that are accessible for oligonucleotide binding. Oligonucleotides that are complementary to these accessible areas were designed and include Z7 (SEQ ID NO:7), Z8 (SEQ ID NO:9), Z9 (SEQ ID NO:11), Z11 (SEQ ID NO:14), N2 (SEQ ID NO:35), N3 (SEQ ID NO:36), and N7 (SEQ ID NO:40).

PS and PO oligonucleotides with random sequences of twenty or twenty five nucleotides were used as negative controls. At each step of the synthesis of the random oligonucleotides, the synthesizer was given the free choice of all four deoxynucleotides, resulting in a random mixture of $4^{25}$ sequences. Two other PS oligonucleotides were also used as negative controls. One of these oligonucleotides has the sequence 5' CT TTG CTG AAG ATG ATG GAC CCA AA 3' (SEQ ID NO:63), which is complementary to the sequence of the Z1 oligonucleotide (SEQ ID NO:1). The other oligonucleotide has the sequence 5' GA AAC GAC TTC TAC TAC CTG GGT TT 3' (SEQ ID NO:62), which is the reverse of the sequence of the Z1 oligonucleotide (SEQ ID NO:1).

After synthesis, all oligonucleotides were dissolved in water and stored at −20° C. The solvent used in the synthesis of the oligonucleotides had no inhibitory effect on induction of EBV antigens or linear EBV DNA.

Oligonucleotide Treatment of Cells

Logarithmically growing Akata cells were resuspended to a final concentration of $1\times10^6$ cells/ml in fresh medium. The cells were incubated in the presence of various concentrations of oligonucleotides for 3 hours at 37° C., and then exposed to anti-human IgG antibodies (Cappel, West Chester, Pa.) at a concentration of 100 µg/ml for 24 hours in the continued presence of the oligonucleotides.

Transfection Reagents

In some experiments, the cells were treated with transfection reagents prior to incubation with the oligonucleotides. In these experiments, 1 ml of OptiMEM I™ medium (Gibco/BRL) was added to each well of a 6 well plate (Corning). The lipofectin derivative DMRIE-C™ (DC) (Gibco/BRL) was added to each well. The oligonucleotides were added to the wells, and after swirling to mix, the plate was incubated for 15–45 min. at room temperature. Akata cells ($3\times10^6$) in 200 µl OptiMEM I were then added to each well. After gentle mixing, the plates were incubated for 4 hours in a 37° C. $CO_2$ incubator. After the incubation, 1 ml of RPMI 1640 containing 20% Fetal Calf Serum (FCS) was added to each well, followed by 100 µg/ml antibody to IgG.

Liposomes

Methods of preparing liposomes and microspheres for administration to a patient are known to those skilled in the art. For example, U.S. Pat. No. 4,789,734 describes methods for encapsulating biological materials in liposomes. The material is dissolved in an aqueous solution, the appropriate phospholipids and lipids are added, along with surfactants, if required, and the material is dialyzed or sonicated, as necessary. A review of known methods is provided by Gregoriadis, *Drug Carriers in Biology and Medicine*, pp. 287–341 (Academic Press, 1979).

Polymer microspheres are well known to those skilled in the art, and can be tailored for passage through the gastrointestinal tract directly into the bloodstream. Alternatively, the oligomers or their derivatives can be incorporated into microspheres, and implanted for slow release over a period of time. See, e.g., U.S. Pat. Nos. 4,925,673 and 3,625,214.

Incorporation of $^3$H-Thymidine

Akata cells ($2\times10^6$), either stimulated with antibody to IgG, or unstimulated, were incubated with oligonucleotides for 24 hours. The cells were then incubated with 1 µCi of $^3$H-thymidine (New England Nuclear/duPont) for 4 hours at 37° C., and lysed with 0.4 M NaOH. The lysates were harvested onto fiberglass filters and washed extensively. The filters were allowed to dry and subjected to scintillation counting.

P3HR-1 cells ($1\times10^6$) were incubated with oligonucleotides at 33° C. At two day intervals, the cells were counted and adjusted to $1\times10^6$ cells/ml by adding fresh medium containing the original concentration of oligonucleotides. The cells were maintained in this manner for up to 18 days. Aliquots were taken for EBV DNA analysis and immunofluorescence at various time points.

EBV DNA Analysis

EBV DNA in the infected cells was analyzed by the method described in Gardella et al., *J. Virol.* 50: 248–254 (1984). This technique allows the resolution of linear and circular viral DNA in EBV-infected cells. Briefly, Akata cells (0.5×10⁶) or P3HR-1 cells (1.0×10⁶) were suspended in 100 μl of sample buffer containing 15% Ficoll and 0.01% bromophenol blue in TBE buffer (89 mM Tris, 89 mM boric acid, 2.5 mM EDTA, pH 8.3) and loaded into the well of a vertical 0.75% agarose gel. Lysis buffer (100 μl) containing 5% Ficoll, 1% sodium dodecyl sulfate (SDS), pronase (1.5 mg/ml), and 0.05% xylene cyanol green in TBE buffer, was layered over the samples. Electrophoresis was carried out at 4° C. at 20 V for 3 hours and then at 80 V for 16 hours at 4° C. The DNA in the gel was partially depurinated with 0.25 M HCl, denatured with 0.4 M NaOH in 0.5 M NaCl, and transferred to nylon-membrane filters (MagnaCharge; Micron Separation Inc., Westboro, Mass.) using downward capillary alkaline transfer. The filters were baked at 80° C. for 1 hour, treated with prehybridization buffer containing 50% formamide at 42° C., and hybridized to an EBV-specific probe in hybridization buffer containing 50% formamide at 42° C. The probe used was a DNA fragment derived from the BamHI W region of the EBV genome, which was labelled with $^{32}$p by the random priming method. The filters were washed in 0.1×SSC at 60° C., dried and exposed to Kodak XAR films at −80° C. with intensifying screens. The amount of linear EBV DNA present on the filters was quantitated with a bioimage analyzer (Betagen, Intelligenetics, Inc., Mountain View, Calif.).

Indirect Immunofluorescence

Indirect immunofluorescence was used for staining diffuse early antigen (EA-D) and viral capsid antigen (VCA). EA was detected with serum from a patient with NPC (EA titer, 1:320; VCA titer, 1:320). VCA was detected with serum from healthy seropositive donor (VCA titer, 1:160; EA titer, less than 1:10) from a healthy donor (Daibata et al., 1990). Cells were washed with phosphate buffered saline (PBS) and spotted on a glass slide, dried, and fixed in acetone at −20° C. for 15 minutes. The fixed smears were incubated with anti-EA or anti-VCA antibodies at 37° C. for 40 minutes. The slides were washed with PBS, and incubated with fluorescein isothiocyanate (FITC)-conjugated goat anti-human IgG (Cappel, West Chester, Pa.) at 37° C. for 40 minutes. The slides were washed and mounted in 1:1 glycerol/PBS, and examined under a fluorescence microscope. At least 500 cells were counted for each determination.

Fluorescence Activated Cell Sorting (FACS)

Cells (1×10⁶) were washed and resuspended in 200 μl PBS and incubated at room temperature for twenty minutes. Ortho Permafix (Ortho Diagnostic Systems, Raritan, N.J.) (0.4 ml) was added and after vortexing the cells were incubated for forty minutes at room temperature. The cells were then centrifuged at 1000×g for five minutes at room temperature, resuspended in 2 ml of wash buffer (25 ml FCS, 7.5 g bovine serum albumin (BSA), and 27.5 mg disodium EDTA in 500 ml PBS) and incubated for ten minutes at room temperature. The cells were again centrifuged as above, and the supernatant was decanted.

EA-D, the BMRF1 gene product, was detected with marine IgG₁ monoclonal antibody (mAb) 9240 (New England Nuclear/duPont, Wilmington, Del.). The antibody (10 μl) was added to the cells, and after vortexing the cells were incubated for forty minutes at room temperature. The cells were then washed in wash buffer and centrifuged. The supernatant was decanted and FITC-conjugated goat anti-mouse Ig (diluted 1:5) (Cappel, West Chester, Pa.) was added to the cells. After vortexing, the cells were incubated for forty minutes at room temperature. The cells were then washed twice in wash buffer and centrifuged. The supernatant was decanted and the cells were resuspended in 0.5 ml PBS and analyzed immediately, or in 0.5 ml post-fix (1.1% paraformaldehyde in PBS) and stored for later analysis. Post-fixed cells were stable for several weeks at 4° C. Cells were analyzed on a FACScan using FACScan Research Software Version 2.1.

Western Blot Analysis

ZEBRA protein was detected by Western blotting using a rabbit polyclonal antibody, as described in Taylor et al., *J. Virol.* 63: 1721–1728 (1989). This antibody recognizes; a 38 kD ZEBRA protein in Akata cells after crosslinking with anti-IgG. The cells were washed in PBS and resuspended in lysis buffer containing 10 mM Tris-HCl (pH 7.2), 150 mM NaCl, 1% Triton X-100, 0.1% SDS, 0.5% sodium deoxycholate, 2 mM phenylmethylsulfonyl fluoride and 1 μg/ml aprotonin for twenty minutes on ice. After sonication, the lysates were centrifuged at 15000×g at 4° C. and the supernatants were collected. Each sample was diluted with an equal volume of 2×SDS sample buffer (125 mM Tris-HCl, pH 6.8, 4.6% SDS, 10% 2-mercaptoethanol, 20% glycerol), heated to 100° C. for 5 minutes, and electrophoresed on 10% SDS-PAGE gels. The proteins were electrophoretically transferred onto nitrocellulose filters (Hybond-C; Amersham, Arlington Heights, Ill.), in transfer buffer (25mM Tris, 192 mM glycine, 20% methanol, pH 8.3) at 100 V for 2 hours at constant voltage. Residual binding sites on the nitrocellulose filters were blocked for 1 hour with Tris-buffered saline (20 mM Tris-HCl, 500 mM NaCl, pH 7.5) containing 3% gelatin. The filter was incubated overnight with a 1:200 dilution of the antibody to ZEBRA in Tris-buffered saline plus 0.05% Tween 20 in the presence of 1% gelatin followed by incubation with $^{125}$I protein A (New England Nuclear/duPont). The filters were exposed to Kodak XAR films. The amount of ZEBRA was quantitated with a PhosphorImager (Molecular Dynamics, Sunnyvale, Calif.).

In vitro Models

A model system for the study of EBV latency is based on the infection of resting peripheral blood B lymphocytes in vitro. Cells infected in this manner express the viral proteins associated with latency and become "immortalized," i.e., they proliferate indefinitely. B cells derived from certain tumors such as EBV-positive BLs are also immortalized and have been adapted to grow in vitro. Such cells are treated with EBV antisense oligonucleotides to evaluate the ability of these oligonucleotides to inhibit EBV replication and/or gene expression.

The ability of antisense oligonucleotides to inhibit functions associated with the EBV lytic cycle is evaluated by administering the oligonucleotides to certain cultured B cell lines that are undergoing lytic infection. One such cell line is the BL-derived P3HR-1, in which a high percentage of cells spontaneously enters the lytic cycle. Another cell line that can be used to evaluate the ability of antisense oligonucleotides to inhibit EBV functions is the Akata cell line, which in the absence of stimulation maintains the virus in a latent state, but upon cross-linking of its surface immunoglobulin receptor is induced to enter the EBV lytic cycle (Takada et al., *J. Virol.* 63: 1721–1728 (1989)).

The results in these in vitro models can be used to estimate the effectiveness of a particular oligonucleotide to inhibit EBV function in vivo, e.g., in a mammal.

Animal Models

The host range of EBV is essentially limited to certain types of human cells. However, if lymphocytes from an EBV-seropositive donor are introduced into certain immunosuppressed mice, e.g., SCID (Severe Combined Immunodeficiency) mice, the human EBV-infected cells will form tumors in the mice that are similar to the EBV-associated tumors observed in humans who are immunosuppressed, e.g., due to HIV infection or cyclosporin A treatment associated with organ transplantation. Mosier et al., *Current Topics Micro. Immunol.*, pp. 317–323 (1990).

SCID mice with EBV-infected B cell lymphomas can be treated with antisense oligonucleotides specific for EBV genes. Protocols for reconstituting SCID mice with human EBV-infected cells have been previously described in detail. Id. Briefly, blood samples are taken from healthy EBV-seropositive individuals or from acute infectious mononucleosis (IM) patients within five days from the first positive monospot test for heterophile antibodies. Human peripheral blood mononuclear cells (huPBMC) are obtained from the samples by density gradient centrifugation over Ficoll-Hypaque (Pharmacia). The huPBMC are washed in PBS and resuspended at $1\times10^8$ per ml. Within two hours of their isolation, $5$–$6\times10^7$ huPBMC are injected intraperitoneally into six to twelve week old SCID mice, e.g., C.B.17-scid/scid (bred and housed in a facility at University of Massachusetts Medical Center, Worcester, Mass.). Successful reconstitution of the mice with the human cells is tested by evaluating the mice for the expression of human Ig. Mice that have been reconstituted successfully are followed for the development of, e.g., lymphoproliferative disease of human B cells (BLPD). The development of BLPD is assessed by measuring tumor load or the amount of human Ig secreted.

Antisense oligonucleotides are administered to mice intraperitoneally at a dose of 100 mg/kg of body weight once a day. See, e.g., Dean et al., *Proc. Natl. Acad. Sci. (USA)* 91: 11762–11766 (1994). Successful treatment with antisense oligonucleotides is reflected in a lower percentage of mice developing BLPD, or in a later onset of BLPD than in control mice that are not given oligonucleotides.

The results in these in vivo models can be used to evaluate the expected effectiveness of a particular oligonucleotide to treat a person for a specific disease associated with a particular EBV gene.

Methods of Administration

The antisense oligonucleotides can be administered as individual therapeutic agents or in combination with other therapeutic agents. They can be administered alone, but are generally administered with a pharmaceutically acceptable carrier selected on the basis of the chosen route of administration and standard pharmaceutical practice. The dosage administered will vary depending upon known pharmacokinetic/pharmacodynamic characteristics of the particular agent and its mode and route of administration, as well as the age, weight, and health of the recipient, the nature and extent of disease, kind of concurrent therapy, frequency and duration of treatment and the effect desired.

A typical dose is about 1 to 10 mg, preferably about 3 mg, of oligonucleotide per kilogram of body weight per day, by continuous intravenous infusion or as a bolus. Dosage will vary according to oligonucleotide modifications. Other routes of administration include oral, intradermal, intrathecal, and injection into lymph nodes. The oligonucleotides can be administered as a suppository or transdermal patch. For treatment of NPC, the oligonucleotides can be nebulized and administered as inhalants.

Examples

Inhibition of ZEBRA Expression by BZLF1 Antisense Oligonucleotides

To determine the effect of BZLF1 antisense oligonucleotides on the expression of EBV lytic cycle antigens, the EBV-infected Akata BL cell line was treated with PO or PS Z1 (SEQ ID NO:1) or control oligonucleotides. The cells were then exposed to IgG antibody to induce the EBV lytic cycle. ZEBRA expression was measured in the cells by Western Blotting. While ZEBRA was undetectable in unstimulated cells, after stimulation with antibody to IgG, ZEBRA was abundantly detected as a single band at 38 kD.

ZEBRA expression was suppressed by 70–90% when the cells were treated with PS Z1 (SEQ ID NO:1)at 2.5 to 12.5 $\mu$M. PO Z1 (SEQ ID NO:1) also inhibited ZEBRA expression, but the effect was not as strong. Only low inhibition was observed in cells treated with the same concentration of random oligonucleotides of the same length and nucleotide modification.

To exclude the possibility that the suppression of ZEBRA expression by Z1 oligonucleotides was merely the result of a general suppression of protein synthesis, the expression of the B cell membrane protein CD 19 in the presence or absence of the PS Z1 (SEQ ID NO:1) or control oligonucleotides was determined. CD 19 is a membrane protein with a half-life of 14–16 hours. Its expression was analyzed by FACS using an anti-CD 19 monoclonal antibody. The PS oligonucleotides had no effect on CD 19 expression either before or after anti-IgG stimulation of Akata cells.

Thus, BZLF1 antisense oligonucleotides can inhibit ZEBRA expression, the earliest event in the lytic cycle of EBV, in a sequence-specific, dose-dependent manner.

Inhibition of Expression of Early Viral Antigens by BZLF1 Antisense Oligonucleotides Expression of diffuse Early Antigen (EA-D) was measured by indirect immunofluorescence in Akata cells exposed to Ig antibody in the presence or the absence of BZLF1 oligonucleotides. Representative results, in which these cells were treated with 100 $\mu$g/ml of the oligonucleotides, are shown in FIG. 1.

When no oligonucleotides were added to the cells, over 40% of the cells expressed EA-D (A in FIG. 1). In contrast, in the presence of PS Z1 (SEQ ID NO:1), EA was expressed by only about 17% of the cells (D in FIG. 1). EA-D expression was inhibited to a lesser extent by PO Z1 (SEQ ID NO:1); approximately 25% of the cells treated with this oligonucleotide expressed EA-D (B in FIG. 1). This inhibition was sequence-specific, as treatment with control PS (E) and PO (C) oligonucleotides was not as effective as treatment with oligonucleotides specific for BZLF1 sequences. As shown in FIG. 1, the control PS and PO oligonucleotides resulted in the expression of EA in approximately 28% and 33% of the cells, respectively. Therefore, treatment with antisense oligonucleotides specific for BZLF1 results in a decrease in the expression of a specific marker of early events in lytic EBV infection.

Figure 2A:
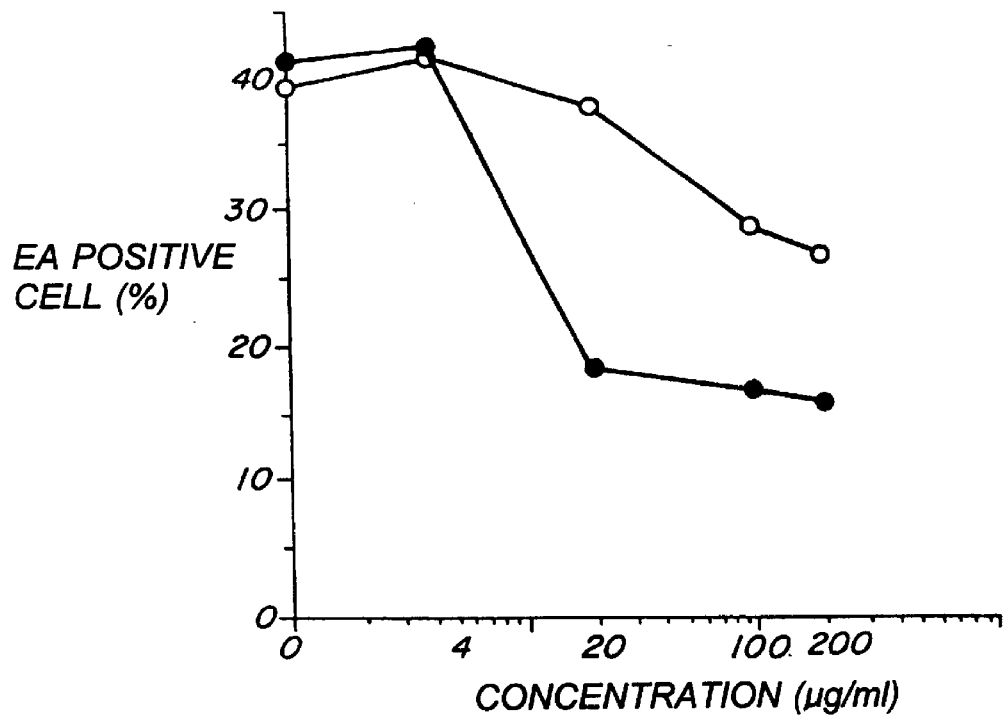
FIG. 2A is a graph showing the levels of EA-D expression after induction of the EBV lytic cycle in Akata cells treated with various concentrations of PS control (-○-) or PS BZLF1 antisense (-●-) oligonucleotides.
Figure 2B:
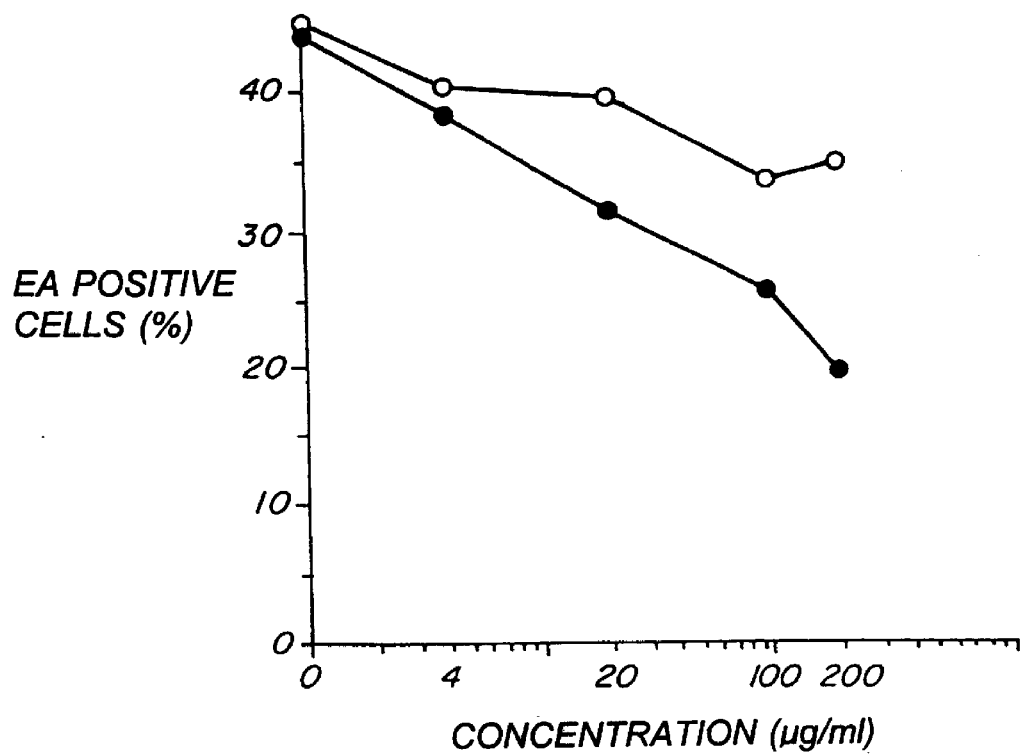
FIG. 2B is a graph showing the levels of EA-D expression after induction of the EBV lytic cycle in Akata cells treated with various concentrations of PO control (-○-) or PO BZLF1 antisense (-●-) oligonucleotides.

The inhibitory effect of these BZLF1 antisense oligonucleotides was dose-dependent. FIG. 2A shows the results obtained with PS Z1 oligonucleotides, and FIG. 2B shows the results obtained using PO Z1 oligonucleotides at a variety of different concentrations. The open circles in the graphs represent control oligonucleotide results; the closed circles represent Z1 oligonucleotide results. As shown in the graphs, addition of 4 $\mu$g/ml PS or PO Z1 (SEQ ID NO:1) oligonucleotides had little or no effect on EA expression. However, when PS Z1 (SEQ ID NO:1) oligonucleotides were used at a concentration of 20 $\mu$g/ml or greater, the level of EA expression was markedly reduced.

The PS Z1 (SEQ ID NO:1) oligonucleotides at 20 $\mu$g/ml had approximately the same inhibitory effect as PO Z1 (SEQ ID NO:1) oligonucleotides at 200 $\mu$g/ml. This result is most likely due to the fact that Po oligonucleotides have a shorter intracellular half-life than PS oligonucleotides.

Thus, in addition to inhibiting ZEBRA expression, BZLF1 antisense oligonucleotides inhibit the expression of EBV Early Antigen in a sequence-specific, dose-dependent manner.

Inhibition of Production of Linear EBV DNA by BZLF1 Antisense Oligonucleotides

In addition to the expression of specific viral proteins such as ZEBRA and EA-D, cells infected with EBV in the lytic phase also are characterized by the presence of intracellular linear EBV DNA. Linear viral DNA is synthesized after the expression of Early Antigens. Therefore, BZLF1 antisense oligonucleotides were tested for their ability to inhibit the production of linear EBV DNA. Akata cells were exposed to antibody to IgG in the presence or absence of PO or PS Z1 (SEQ ID NO:1)oligonucleotides. The amount of lytic EBV DNA was measured using the Gardella gel technique. In this technique, whole EBV-infected cells are lysed in the well of an agarose gel, and subjected to electrophoresis. Linear and circular EBV DNAs enter the gel matrix and are resolved by their differential migration in the gel. The gels are blotted onto nylon membranes, hybridized to EBV-specific probes, and subjected to autoradiography. Linear EBV DNA on the blots is quantitated by Betagen, and is expressed as counts per minute (cpm).

The results of experiments using oligonucleotides PS and PO Z1 (SEQ ID NO:1) are shown in Table II. The Table indicates the cpm obtained when cells were treated with various concentrations of oligonucleotides, and the ratio of cpm to that obtained when the cells were not treated with oligonucleotides. Treatment of Akata cells with 4 µg/ml PO or PS Z1 (SEQ ID NO:1) resulted in no significant inhibition. However, at 20 µg/ml, 100 µg/ml, and 200 µg/ml, PS Z1 (SEQ ID NO:1) oligonucleotides reduced the amount of linear EBV detected by approximately 75%. At 200 µg/ml, PO antisense oligonucleotides reduced the amount of linear EBV DNA by approximately 63%.

PS control oligonucleotides had only a minimal effect on the production of linear EBV DNA, reducing the amount detected by 24% (at 20 µg/ml), −1% (at 100 µg/ml), and 31% (at 200 µg/ml). PO control oligonucleotides had no significant effect on effect on linear EBV production. Thus, in addition to inhibiting the expression of IE and Early EBV genes, BZLF1 antisense oligonucleotides inhibit EBV linear DNA synthesis in a sequence-specific, dose-dependent manner.

PO and PS Z3 (SEQ ID NO:3) oligonucleotides were similar to PO and PS Z1 (SEQ ID NO:1) in their ability to inhibit linear viral DNA production. In contrast, treatment of Akata cells with PO and PS Z2 (SEQ ID NO:2) resulted in only a modest inhibition of linear EBV DNA synthesis, and the addition of Z2 (SEQ ID NO:2) oligonucleotides to the Z3 (SEQ ID NO:3) oligonucleotides did not significantly enhance the level of inhibition observed in cells treated with the Z3 (SEQ ID NO:3) oligonucleotides alone. Similar results were observed at the level of ZEBRA expression.

TABLE II

Effect of the Z1 BZLF1 Oligonucleotide on Linear EBV DNA Synthesis

| Oligo-nucleotide | 4 µg/ml | | 20 µg/ml | | 100 µg/ml | | 200 µg/ml | |
|---|---|---|---|---|---|---|---|---|
| | cpm | ratio | cpm | ratio | cpm | ratio | cpm | ratio |
| None | 39 | 1.00 | 75 | 1.00 | 146 | 1.00 | 88 | 1.00 |
| PS Z1 (SEQ ID NO:1) | 34 | 0.86 | 20 | 0.27 | 33 | 0.23 | 24 | 0.26 |
| PS control | 43 | 1.09 | 57 | 0.76 | 149 | 1.01 | 60 | 0.69 |
| PO Z1 (SEQ ID NO:1) | 47 | 1.20 | 82 | 1.09 | 116 | 0.79 | 32 | 0.37 |
| PO Control | 64 | 1.60 | 78 | 1.04 | 164 | 1.12 | 117 | 1.3 |

Figure 3A:
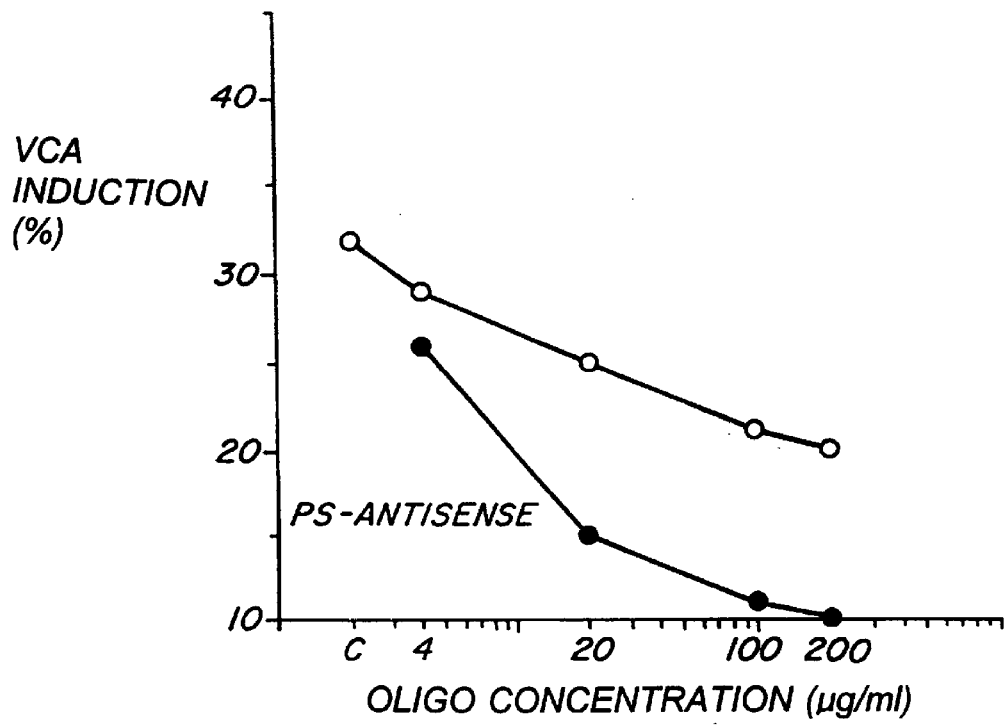
FIG. 3A is a graph showing the levels of expression of the EBV Late gene viral Capsid Antigen (VCA) after induction of the EBV lytic cycle in Akata cells treated with various concentrations of PS control (-○-) or PS BZLF1 antisense (-●-) oligonucleotides.
Figure 3B:
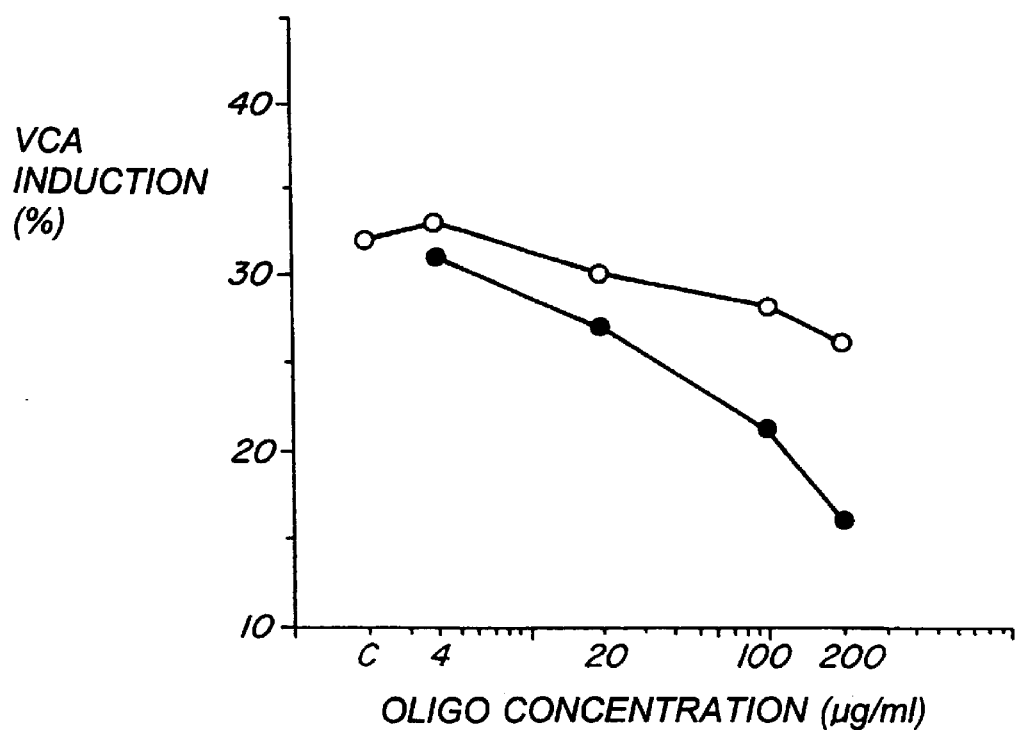
FIG. 3B is a graph showing the levels of VCA expression after induction of the EBV lytic cycle in Akata cells treated with various concentrations of PO control (-○-) or PO BZLF1 antisense (-●-) oligonucleotides.

Inhibition of the Expression of Late Viral Antigens by BZLF1 Antisense Oligonucleotides Another marker of lytic infection is the presence of EBV Late Antigens, such as the Viral Capsid Antigen (VCA), which is expressed subsequent to the replication of linear EBV DNA. VCA expression was measured in Akata cells which were exposed to Ig antibody in the presence or absence of BZLF1 antisense oligonucleotides. FIG. 3A shows the results obtained when the cells were treated with PS Z1 (SEQ ID NO:1)(closed circles) or PS control (open circles) oligonucleotides. A significant decrease in the level of VCA expression is seen when the cells are exposed to 20 µg/ml, 100 µg/ml, or 200 µg/ml PS Z1(SEQ ID NO:1). As shown in the graph, PS control oligonucleotides did not have the same effect on VCA expression levels. FIG. 3B shows the results obtained when the cells were treated with PO Z1 (SEQ ID NO:1)(closed circles) or PO control (open circles) oligonucleotides. While PO Z1 significantly reduced VCA expression, PO control oligonucleotides did not have the same effect. Therefore, BZLF1 antisense oligonucleotides can inhibit VCA expression, a late event in the EBV lytic cycle, in a dose-dependent, sequence-specific manner.

These results are concordant with the results obtained for ZEBRA and Early Antigen Expression and EBV lytic DNA production. PO and PS BZLF1 antisense oligonucleotides can therefore inhibit ZEBRA, as well as downstream viral functions associated with the lytic cycle, including expression of EBV Early Antigens, replication of viral DNA, and expression of EBV Late Antigens, in a sequence-specific and dose-dependent manner.

EBV Inhibition by BZLF1 Antisense Oligonucleotides Added Before Induction of the EBV Lytic Cycle Inhibition of EBV functions by BZLF1 antisense oligonucleotides might be most effective if the oligonucleotides were already present intracellularly at the time of induction of the lytic cycle, because within twenty minutes of induction of the EBV lytic cycle in Akata cells by exposure to Ig antibody, BZLF1 mRNA can be found in the nucleus. Mellinghoff et al., *Virology* 185: 922–928 (1991). Thus, to determine the most effective time to add BZLF1 antisense oligonucleotides, Akata cells were treated with control or BZLF1 antisense oligonucleotides at different times before induction with Ig antibody, and were analyzed on a Gardella gel to determine the effect of the oligonucleotides on lytic viral DNA synthesis.

Figure 4:
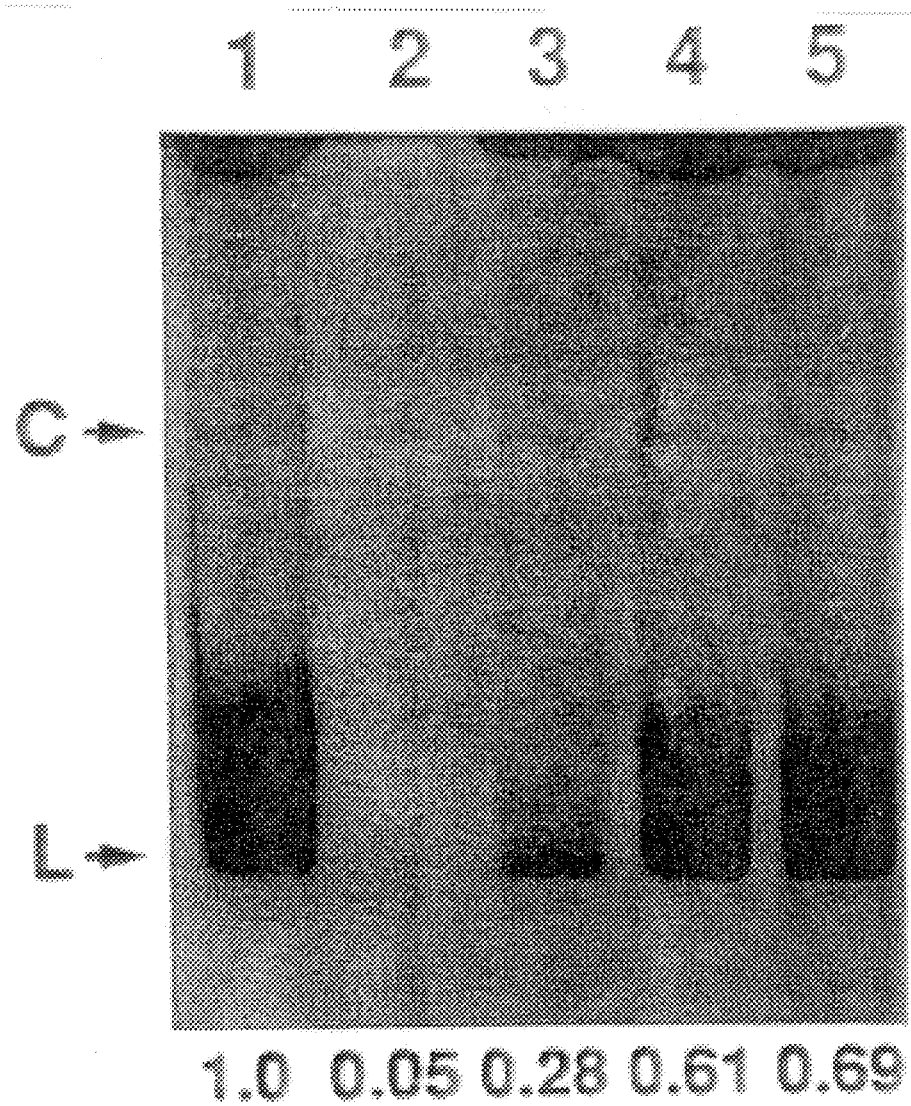
FIG. 4 is an autoradiogram of a Southern blot of a Gardella gel showing the levels of linear EBV DNA present after induction of the EBV lytic cycle in Akata cells treated with PS BZLF1 antisense oligonucleotides before, during or after the time of induction.

The results are shown in FIG. 4. The numbers under each lane represent the ratio of the amount of linear EBV DNA (designated by an L in the figure) detected in that lane to the amount detected in the lane corresponding to Akata cells which had been exposed to antibodies to Ig, but which were not given any oligonucleotide (Lane 1). Lane 2 shows the results when the Akata cells were not treated with Ig antibody, i.e, the cells are not induced to enter the lytic cycle. No significant linear EBV DNA is detected in these cells.

Lanes 3, 4, and 5 show the results when the cells were exposed to PS Z1 three hours before, at the time of, or three hours subsequent to induction by antibody to Ig, respectively.

As shown in the figure, the addition of PS BZLF1 antisense oligonucleotides three hours before induction of the EBV lytic cycle reduces the amount of viral DNA detected by 72% (Lane 3). In contrast, when PS Z1 (SEQ ID NO:1) is added at the time of (Lane 4) or three hours after (Lane 5) induction, only 29% or 21% inhibition, respectively, is observed. Thus, BZLF1 antisense oligonucleotides are most effective when administered prior to the initiation of the lytic cycle.

Inhibition of EBV in P3HR-1 Cells by Continuous Administration of BZLF1 Antisense Oligonucleotides Another cell line that can be used to test the ability of various oligonucleotides to inhibit EBV functions is the BL-derived cell line, P3HR-1. P3HR-1 contains an EBV genome which has sustained a number of deletions, and the lytic viral DNA produced by P3HR-1 cells is defective. P3HR-1 produces this defective linear viral DNA even in the absence of stimulation by exogenous agents. The effect of BZLF1 antisense oligonucleotides on the induction of the EBV lytic cycle and on ongoing viral replication was tested in P3HR-1 cells. The cells were treated with PS Z1 (SEQ ID NO:1)at 100 µg/ml or 200 µg/ml on day 0.

Figure 5A:
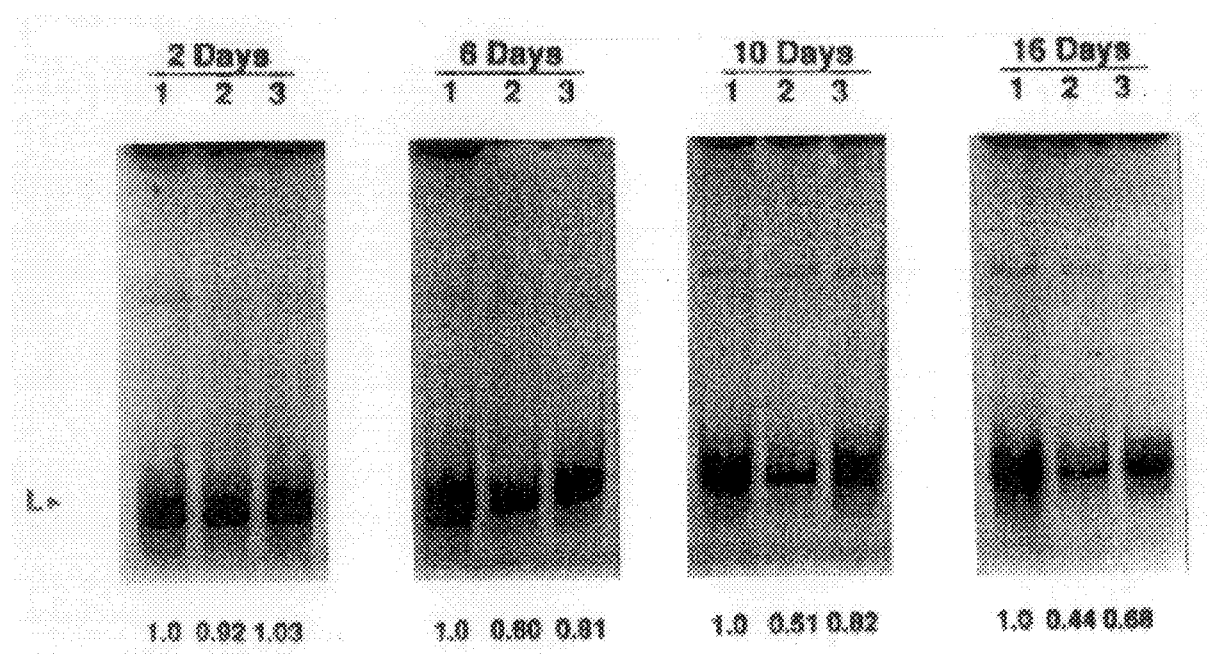
FIG. 5A is an autoradiogram of a Southern blot of a Gardella gel showing the amount of linear EBV DNA detected in P3HR-1 cells treated with 100 μg/ml PS BZLF-1 antisense oligonucleotides for sixteen days.
Figure 5B:
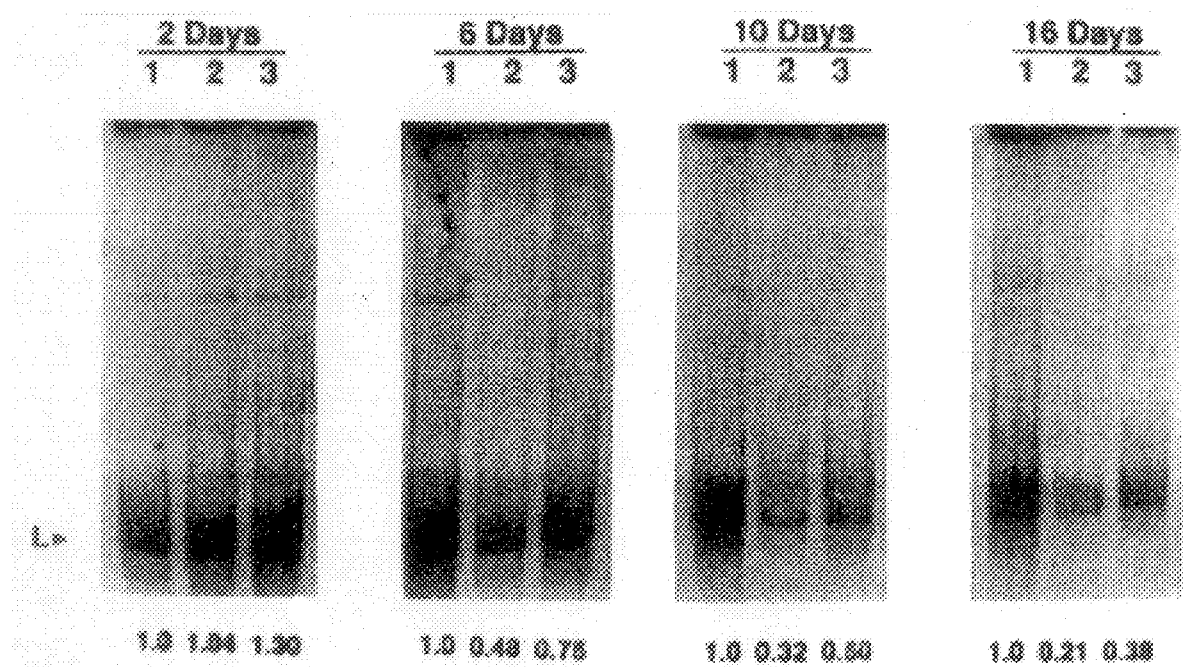
FIG. 5B is an autoradiogram of a Southern blot of a Gardella gel showing the amount of linear EBV DNA detected in P3HR-1 cells treated with 200 μg/ml PS BZLF1 antisense oligonucleotides for sixteen days.

Every two days, oligonucleotides were replenished at the same concentration, for up to eighteen days. The amount of linear EBV DNA in the cells was then quantitated by Gardella gel analysis. The results of representative experiments, in which the cells were treated with PS Z1 (SEQ ID NO:1) oligonucleotides at 100 or 200 µg/ml, are shown in FIGS. 5A and 5B, respectively. In the figures, lanes labelled 1 correspond to cells that were not given oligonucleotides; lanes labelled 2 correspond to cells treated with PS Z1 (SEQ ID NO:1); and lanes labelled 3 correspond to cells treated with PS control oligonucleotides.

The number under each lane represents the amount of linear EBV DNA (labelled "L") in that lane compared to the amount of linear EBV in the corresponding lane 1. Incubation of P3HR-1 cells with PS Z1 (SEQ ID NO:1) oligonucleotides had a marked effect on the amount of linear EBV DNA detected. For example, FIG. 5B shows that the PS Z1 (SEQ ID NO:1) antisense oligonucleotides at a concentration of 200 µg/ml reduced the amount of linear EBV DNA by 52% by day 6, by 68% by day 10, and by 79% by day 16. In contrast, at the same concentration, control oligonucleotides reduced the amount of linear EBV DNA detected by only 25% by day 6, by 50% by day 10, and by only 62% by day 16. Prolonged treatment with PS Z1 (SEQ ID NO:1) also resulted in a reduction of the amount of EA and VCA detected in P3HR-1 cells.

The observed reduction in the amounts of linear EBV DNA induced by the PS random oligonucleotides may be explained by nonspecific inhibition of EBV DNA polymerase by PS oligonucleotides, which has been shown to occur at a low level. Yao et al., *Antimicrob. Agents Chemother.* 37: 1420–1425 (1993). Inhibition by the PS BZLF1 antisense oligonucleotides may be due to a combination of the PS and sequence-specific effects.

To eliminate the possibility that the observed inhibition of EBV functions by BZLF1 antisense oligonucleotides was due to nonspecific cytotoxic effects of the oligonucleotide preparations, incorporation of tritiated thymidine into cells treated with the PS antisense oligonucleotides measured. The amount of thymidine incorporated is an indicator of cellular proliferation; therefore, if the oligonucleotides have a significant cytotoxic effect, thymidine incorporation should be decreased in cells exposed to the oligonucleotides. There were no significant decreases in the levels of thymidine incorporation in the cells exposed to antisense oligonucleotides compared to cells not exposed to oligonucleotides, indicating that the oligonucleotides have no discernible cytotoxic effect.

These studies show that certain BZLF1 antisense oligonucleotides can inhibit the expression of ZEBRA, Early and Late viral antigens, and lytic EBV replication. These antiviral effects are sequence-specific, as indicated by the inability of sense and reverse sequences to inhibit these viral functions to an extent similar to that seen with the antisense oligonucleotides, and dose-dependent. The results indicate that the inhibition of lytic EBV replication is a result of a blockage of ZEBRA synthesis at an early stage of the viral lytic cascade. BZLF1 antisense oligonucleotides are therefore useful in the treatment of diseases associated with progression through the EBV lytic cycle, such as OHL. These oligonucleotides may also be useful in the treatment of ARLs, which express ZEBRA but undergo an abortive EBV lytic cycle. A possible mechanism by which ARLs become tumorigenic is through ZEBRA interaction with p53. Zhang et al., *Mol. Cell. Biol.* 14: 1929–1938 (1994). Inhibition of ZEBRA would make it unable to bind to and inactivate p53.

These results also show that the ZEBRA protein is not produced in great quantity. PO Z1 suppressed ZEBRA synthesis by 60%, and suppressed subsequent events in the viral lytic cycle to a similar degree. If ZEBRA were synthesized in excess, a 60% reduction in expression would not be expected to have any substantial effect on these downstream events.

The observed reduction in detectable linear EBV DNA synthesis due to exposure to BZLF1 antisense oligonucleotides may be due to a reduced amount of Early gene products, whose transcription must be activated by the ZEBRA protein, and which are necessary for viral DNA replication, and a failure to activate orilyt, which requires ZEBRA binding in order to be functional.

EBV Inhibition by Various BZLF1 Antisense Oligonucleotides

A number of other BZLF1 antisense oligonucleotides were synthesized and tested, either alone or in combination with one another, for their ability to inhibit EBV-associated functions. In these experiments, Akata cells were treated with oligonucleotides and then induced to enter the lytic cycle by exposure to antibody to IgG. The cells were then analyzed for EA-D expression by FACS, and/or the presence of linear EBV DNA.

The specific oligonucleotides tested are described in Table I. They include:

5' TTT GGG TC 3' (Z4, SEQ ID NO:4);
5' TTT GGG TCT CTC TTT GGG TC 3' (Z5, SEQ ID NO:5);
5' TTT GGG TCN NNN NNN NNN NN 3' (Z6, SEQ ID NO:6);
5' AAA TTT TAC ATC TTC AGA 3' (Z7, SEQ ID NO:7);
5' CAG CAC ACA AGG CAA AGG AG 3' (Z8, SEQ ID NO:9);
5' CAG GCT GAG GGG CAG GAA AC 3' (Z10, SEQ ID NO:13);
5' CCC TCC TTA CCG ATT CTG GC 3' (Z11, SEQ ID NO:14);
5' ATT CCT CCA GCT GCG AGC AA 3' (Z12, SEQ ID NO:16);

5' ATA TAC TGA CCT CAC GGT AG 3' (Z13, SEQ ID NO:17); and

5' CAG AAG CCA CCT GCG CAC AA 3' (Z14, SEQ ID NO:18), where "N" denotes a randomly selected nucleotide. PS oligonucleotides were used in all of these experiments.

As shown in Table IIIA, Experiment 1, PS Z5 (SEQ ID NO:5)and Z6 (SEQ ID NO:6) oligonucleotides at a concentration of 25 μM inhibited linear EBV DNA synthesis to a greater extent than the control oligonucleotides. In contrast, the Z4 (SEQ ID NO:4) oligonucleotide showed less inhibition than the control at the same concentration.

TABLE IIIA

Inhibition of linear EBV DNA production by PS BZLF1 Antisense Oligonucleotides

| Oligonucleotides | % Inhibition |
|---|---|
| Experiment 1 | |
| Z4 (SEQ ID NO:4) | 5.1% |
| Z5 (SEQ ID NO:5) | 57% |
| Z6 (SEQ ID NO:6) | 44% |
| PS control | 30% |
| Experiment 2 | |
| Z1 (SEQ ID NO:1) | 44% |
| Z7 (SEQ ID NO:7) | 41% |
| Z1 (SEQ ID NO:1) + Z7 (SEQ ID NO:7) | 66% |
| Z11 (SEQ ID NO:14) + Z12 (SEQ ID NO:16) | 52% |
| R20 (PS control) | 23% |
| Experiment 3 | |
| Z1 (SEQ ID NO:1) | 75% |
| Z7 (SEQ ID NO:7) | 49% |
| Z8 (SEQ ID NO:9) | 37% |
| Z10 (SEQ ID NO:13) | 35% |
| Z11 (SEQ ID NO:14) | 77% |
| R20 | 54% |
| Experiment 4 | |
| Z1 (SEQ ID NO:1) | 57% |
| Z1 (SEQ ID NO:1) + Z11 (SEQ ID NO:14) + Z12 (SEQ ID NO:16) | 71% |
| Z1 (SEQ ID NO:1) + Z13 (SEQ ID NO:17) + Z14 (SEQ ID NO:18) | 69% |
| Z1 (SEQ ID NO:1) + Z7 (SEQ ID NO:7) + Z8 (SEQ ID NO:9) | 73% |
| R20 | 27.1% |

Another oligonucleotide that can decrease linear EBV DNA production is Z7 (SEQ ID NO:7). While PS Z7 (SEQ ID NO:7) did not show significant inhibition in Experiment 3 (see Table IIIA), PS Z7 (SEQ ID NO:7) at 25 μM inhibited linear EBV DNA production by 41%, approximately the same as PS Z1 (SEQ ID NO:1)(44%) at the same concentration (Table IIIA, Experiment 2).

Moreover, the combination of Z1 (SEQ ID NO:1) and Z7(SEQ ID NO:7), each added at a concentration of 25 μM, inhibited linear EBV production by 66%, which is greater than either of these oligonucleotides used alone (see Table IIIA, Experiment 2). Since the concentration of oligonucleotides when using both Z1 (SEQ ID NO:1) and Z7 (SEQ ID NO:7) was twice that when using either alone, the increase in inhibition could be due to either an increased PS effect, increased sequence-specific effects, or both.

The Z1 (SEQ ID NO:1) and Z7 (SEQ ID NO:7) combination was also tested for its ability to decrease EA-D expression. In these experiments, EA-D expression was measured by FACS. Table IIIB shows that while PS Z1 (SEQ ID NO:1)was capable of inhibiting EA expression by 27%, Z7 inhibited EA expression by only 10%. However, the combination of Z1 (SEQ ID NO:1) and Z7 (SEQ ID NO:7) reduced EA expression by 45%. In contrast, the PS control oligonucleotide R20 exhibited no detectable effect on EA expression. Therefore, the combination of Z1 (SEQ ID NO:1) and Z7 (SEQ ID NO:7) exhibited increased inhibition over that seen with the Z1 (SEQ ID NO:1) oligonucleotide alone, as measured by Early Antigen (EA-D) expression and the presence of linear EBV DNA.

TABLE IIIB

Inhibition of linear EBV DNA production by PS BZLF1 Antisense Oligonucleotides

| Oligonucleotides | % Inhibition |
|---|---|
| Z1 (SEQ ID NO:1) | 27% |
| Z7 (SEQ ID NO:7) | 10% |
| Z1 (SEQ ID NO:1) + Z7 (SEQ ID NO:7) | 45% |
| Z11 (SEQ ID NO:14) + Z12 (SEQ ID NO:16) | 32% |
| R20 (PS control) | 0.3% |

PS Z1 (SEQ ID NO:14) alone also inhibited linear EBV DNA synthesis to approximately the same level as Z1 (SEQ ID NO:1) (Table IIIA, Experiment 3). The combination of PS Z11 (SEQ ID NO:14) and Z12(SEQ ID NO:16), each added at a concentration of 25 μM, inhibited linear EBV DNA synthesis by 52% (Table IIIA, Experiment 2). This combination also showed a significant inhibitory effect on EA expression, reducing it by 32%, as compared to Z1 (SEQ ID NO:1) alone at 25 μM, which inhibited EA expression by 27% (Table IIIB). The addition of PS Z1 (SEQ ID NO:14) and Z12 (SEQ ID NO:16) to Z1 (SEQ ID NO:1) (a total oligonucleotide concentration of 75 μM) also increased the inhibition of linear EBV DNA production from 57% to 71% (Table IIIA, Experiment 4). Thus, Z11 (SEQ ID NO:14) either alone or in combination with other oligonucleotides can inhibit EBV functions. Addition of PS Z13 (SEQ ID NO:17) and Z14 (SEQ ID NO:18) to Z1 (SEQ ID NO:1) increased inhibition from 57% to 69%; addition of PS Z7 (SEQ ID NO:8)and Z8 (SEQ ID NO:9) to Z1 (SEQ ID NO:1) increased inhibition from 57% to 73% (Table IIIA, Experiment 4). Therefore, using a combination of two or more BZLF1 antisense oligonucleotides can increase effectiveness in inhibiting EBV functions.

These results indicate that the Z5(SEQ ID NO:5), Z6(SEQ ID NO:6), Z7 (SEQ ID NO:7) and Z11 (SEQ ID NO:14) oligonucleotides can inhibit EBV functions to a similar degree as the Z1 (SEQ ID NO:1) and Z3 (SEQ ID NO:3) oligonucleotides. Various combinations of these oligonucleotides with Z8(SEQ ID NO:9), Z12(SEQ ID NO:16), Z13 (SEQ ID NO:17)and/or Z14 (SEQ ID NO:18) increase these inhibitory effects.

The results also show that while the PS control, R20, a random oligonucleotide of twenty nucleotides, did not inhibit EA expression, it did inhibit linear EBV DNA production by 23%, 54% and 27% in different experiments (see Table IIIA). This finding is consistent with previously observed inhibitory effects of PS oligonucleotides. Yao et al., *Antimicrob. Agents Chemother.* 37: 1420–1425 (1993).

While these BZLF1 antisense oligonucleotides may operate by binding to the RNA encoding ZEBRA, thereby inhibiting ZEBRA translation, sequence-specific oligonucleotides which inhibit viral functions do not always work in this fashion (Fennewald et al., *Antiviral Res.* 1995), and distinct mechanisms may be responsible for the observed effect of the antisense oligonucleotides.

EBV Inhibition by BRLF1 Antisense Oligonucleotides

ZEBRA is a transactivating protein which is the first viral protein expressed upon induction of the EBV lytic cycle. After initiation of the lytic cycle, ZEBRA activates the expression of the immediate early EBV gene BRLF1, which also encodes a transactivator. The BRLF1 gene product and ZEBRA then act in concert to initiate further events in the viral lytic cycle. BRLF1 antisense oligonucleotides were therefore tested for their ability to inhibit viral functions, either alone or in combination with BZLF1 antisense oligonucleotides.

The BRLF1 antisense oligonucleotide R1 has the sequence 5' AT CCT TTT TAG GCC TCA TGG CTA GTA GTA A 3' (SEQ ID NO:19) (see Table I). R1 is complementary to nucleotides 105,166 to 105,195 of the prototype B95-8 strain of EBV (Baer et al., Nature 310: 207–211 (1984)), which contains part of the second exon of BRLF1 and extends into the first intron of the gene. This oligonucleotide was tested for its ability to inhibit EBV functions.

The lytic cycle was induced in Akata cells exposed to different concentrations of various oligonucleotides, and the amount of linear EBV DNA was measured. As shown in Table IV, exposure to PO R1 resulted in an 18% inhibition in the amount of linear EBV DNA detected. This amount of inhibition was less than that seen in cells exposed to 25 $\mu$M PS Z1(SEQ ID NO:1), which showed 57% inhibition. Cells exposed to a lower concentration of PS Z1 (SEQ ID NO:1), 12.5 $\mu$M, showed only 32% inhibition. However, when cells were exposed to both 12.5 $\mu$M PS Z1 and 25 $\mu$M PO R1 (SEQ ID NO:19), a synergistic effect was observed. Linear DNA synthesis was inhibited by 64%. In these experiments, PO rather than PS R1 (SEQ ID NO:19) was used in order to avoid possible additive effects of nonspecific PS inhibition. Thus, the combination of antisense oligonucleotides to the BZLF1 gene encoding the ZEBRA transactivator, and antisense oligonucleotides to BRLF1, an immediate early gene which is transactivated by the ZEBRA protein, is more effective in inhibiting EBV functions than antisense oligonucleotides specific for either BZLF1 or BRLF1 alone.

TABLE IV

Inhibition of Linear EBV DNA Production in
Cells Treated with Antisense Oligonucleotides

| Oligonucleotides added | % Inhibition |
|---|---|
| uninduced Akata cells; no oligonucleotides | 100 |
| induced Akata cells; no oligonucleotides | 0 |
| PS Z1 (SEQ ID NO:1) (25 $\mu$M) | 57 |
| PS Z1 (SEQ ID NO:1) (12.5 $\mu$M) | 32 |
| PO R1 (SEQ ID NO:19) (25 $\mu$M) | 18 |
| PO R1 (SEQ ID NO:19) (25 $\mu$M) + PS Z1 (SEQ ID NO:1) (12.5 $\mu$M) | 64 |
| control (PS-reverse Z1 (SEQ ID NO:1), 12.5 $\mu$M) | 10 |
| control (PS-reverse Z1 (SEQ ID NO:1), 25 $\mu$M) | 28 |

Increased EBV Inhibition by Transfection Reagents

It has been observed that transfection reagents can increase the effectiveness of antisense oligonucleotides in vitro assays. Dean et al., Proc. Natl. Acad. Sci. 91: 11762–11766 (1994). Therefore, the effect of transfection reagents on the ability of the oligonucleotides to inhibit EBV functions was assessed. Akata cells were incubated with various amounts of the DC transfection reagent and 25 $\mu$M PS Z6 (SEQ ID NO:16) (see Table I) oligonucleotides, and then induced to enter the lytic cycle. The amount of linear EBV DNA in the cells was then measured. The results are shown in Table V.

The use of 1 $\mu$l of DC increased inhibition by 32%, and 2–6 $\mu$l increased inhibition between 49 and 75%. Therefore, transfection reagents can increase the effectiveness of the oligonucleotides in inhibiting EBV functions.

TABLE V

Increased Inhibition of EBV DNA Synthesis
by PS Z6 (SEQ ID NO:6) BZLF1
Antisense Oligonucleotide Using Transfection Reagents

| Transfection Reagent ($\mu$l) | cpm | Increase in Inhibition |
|---|---|---|
| 0 | 613 | 0 |
| 1 | 417 | 32% |
| 2 | 311 | 49% |
| 4 | 154 | 75% |
| 6 | 206 | 67% |
| 6 | 221 | 64% |

The use of transfection reagents can also decrease the amount of oligonucleotide necessary to obtain an effective inhibitory response. DC (2 or 3 $\mu$l) was added to Akata cells just prior to addition of 1 or 2.5 $\mu$M PS Z1 (SEQ ID NO:1) or Z6(SEQ ID NO:6). The EBV lytic cycle was induced in the cells, and the amount of linear EBV DNA was measured. The results are shown in Table VI.

In the presence of 2 $\mu$l DC, PS Z1 (SEQ ID NO:1) did not show greater inhibition than the PS control oligonucleotide at 2.5 $\mu$M in the presence of 3 $\mu$l DC (PS Z1 (SEQ ID NO:1), 46%; PS control, 47%). However, if the amount of DC was increased to 3 $\mu$l, inhibition was increased to 87%. PS Z1 (SEQ ID NO:1) at 2.5 $\mu$M in the presence of 2 $\mu$l DC showed inhibition of 62%; in the presence of 3 $\mu$l DC, the inhibition was 94%. PS Z6 (SEQ ID NO:6) at 1 $\mu$M in the presence of 2 $\mu$l DC showed 73% inhibition. Thus, the use of transfection reagents can decrease by twenty-five-fold the concentration of oligonucleotide needed for an effective response.

TABLE VI

Effect of Transfection Reagents on Inhibition of
Linear EBV DNA Synthesis

| Oligonucleotide | Transfection Reagent ($\mu$l) | Inhibition |
|---|---|---|
| PS Z1 (SEQ ID NO:1) (1 $\mu$M) | 2 | 46% |
| PS Z1 (SEQ ID NO:1) (1 $\mu$M) | 3 | 87% |
| PS Z1 (SEQ ID NO:1) (2.5 $\mu$M) | 2 | 62% |
| PS Z1 (SEQ ID NO:1) (2.5 $\mu$M) | 3 | 94% |
| PS Z6 (SEQ ID NO:6) (1 $\mu$M) | 2 | 73% |
| PS control (2.5 $\mu$M) | 3 | 47% |

It may be possible to reduce the amount of oligonucleotide needed for an effective response even further. Table VII shows the effect of using 2 $\mu$l DC on inhibition of linear EBV DNA synthesis by various concentrations of PO and PS oligonucleotides. Both PO and PS Z1 (SEQ ID NO:1) showed significant inhibition at only 1 $\mu$M. By increasing the amount of DC to 3 $\mu$l, it may be possible to decrease the amount of oligonucleotide needed for an effective response even further. It should be noted, however, that in some systems, while the use of transfection reagents is required for effective inhibition by antisense oligonucleotides in vitro, these reagents are not necessary for effective inhibition in vivo. Dean et al., Proc. Natl. Acad. Sci. 91: 11762–11766 (1994).

TABLE VII

Effect of Transfection Reagents on Effective Amount of BZLF1 Antisense Oligonucleotides

| Concentration OF PS Z1 (SEQ ID NO:1) | Inhibition of Linear EBV DNA Synthesis |
|---|---|
| 0.1 μM | 7% |
| 0.3 μM | 28% |
| 1.0 μM | 55% |

Other Embodiments

It is to be understood that while the invention has been described in conjunction with the detailed description thereof, that the foregoing description is intended to illustrate and not limit the scope of the invention, which is defined by the scope of the appended claims. Other aspects, advantages, and modifications are within the scope of the following claims.

TABLE I

| Oligonucleotide | Antisense to | EBV genome (B95-8) coordinates (nucleotides; 5'-3') | Sequence | SEQ ID No. |
|---|---|---|---|---|
| Z1 | BZLF1 | 103, 142–103, 166 (AUG Region) | 5' TTT GGG TCC ATC ATC TTC AGC AAA G 3' | 1 |
| Z2 | BZLF1 | 103, 150–103, 169 | 5' CAT CAT CTT CAG CAA AGA TA 3' | 2 |
| Z3 | BZLF1 | 103, 130–103, 142 (AUG Region) | 5' TCA GAA GTC GAG TTT GGG TC 3' | 3 |
| Z4 | BZLF1 | 103, 159–103, 166 | 5' TTT GGG TC 3' | 4 |
| Z5 | BZLF1 | 103, 159–103, 166;103, 159–103, 166 | 5' TTT GGG TCT CTC TTT GGG TC 3' | 5 |
| Z6 | BZLF1 | 103, 159–103, 166; 11N | 5' TTT GGG TCN NNN NNN NNN NN 3'* *N denotes randomly selected nucleotide | 6 |
| Z7 | BZLF1 | 103, 117–103, 134 (identified by RNAse H assay) | 5' AAA TTT TAC ATC TTC AGA 3' | 7 |
| Z7–40 | BZLF1 | 103, 106–103, 145 | 5' GG GTC AGG TGT AAA TTT TAC ATC TTC AGA AGT CGA GTT TG 3' | 8 |
| Z8 | BZLF1 | 103, 012–103, 031 (identified by RNAse H assay) | 5' CAG CAC ACA AGG CAA AGG AG 3' | 9 |
| Z8–40 | BZLF1 | 103, 002–103, 041 | 5' G CAC CGG CCA CAG CAC ACA AGG CAA AGG AGC TTG CGA TGG 3' | 10 |
| Z9 | BZLF1 | 102, 994–103, 013 (identified by RNAse H assay) | 5' CTC TGG CAG CAC CGG CCA CA 3' | 11 |
| Z9–40 | BZLF1 | 102, 984–103, 023 | 5' G TGG CAG AGG CTC TGG CAG CAC CGG CCA CAG CAC ACA AGG 3' | 12 |
| Z10 | BZLF1 | 102, 915–102, 934 | 5' CAG GCT GAG GGG CAG GAA AC 3' | 13 |
| Z11 | BZLF1 | *102, 648–102,664 | 5' CCC TCC TTA CCG ATT CTG GC 3' | 14 |
| Z11–40 | BZLF1 | *102, 648–102, 674 (splice site) | 5' C TCC TTG ATC CCC TCC TTA CCG ATT CTG GCT GTA GTG GTT 3' | 15 |
| Z12 | BZLF1 | 102, 521–102, 540 (splice site) | 5' ATT CCT CCA GCT GCG AGC AA 3' | 16 |
| Z13 | BZLF1 | 102, 415–102, 434 (splice site) | 5' ATA TAC TGA CCT CAC GGT AG 3' | 17 |
| Z14 | BZLF1 | 102, 330–102, 349 (splice site) | 5' CAG AAG CCA CCT GCG CAC AA 3' | 18 |
| *denotes that Akata sequence includes sequences not found in B95-8 counterpart. | | | | |
| R1 | BRLF1 | 105, 166–105, 195 (AUG; exon 2; intron 1) | 5' AT CCT TTT TAG GCC TCA TGG CTA GTA GTA A 3' | 19 |
| R1–40 | BRLF1 | 105, 166–105, 205 (AUG; exon 2; intron 1) | 5' AT CCT TTT TAG GCC TCA TGG CTA GTA GTA ACA GAG GAA AT 3' | 20 |
| R2 | BRLF1 | 105, 166–105, 185; 106, 127–146 (AUG in spliced message) | 5' AT CCT TTT TAG GCC TCA TGG TGC GTC TGT TTG TGT AGT GA 3' | 21 |
| R3 | BRLF1 | 106, 107–106, 146 (splice site in exon 1 to intron 1) | 5' AC AAA TAA ATT TCT CTT ACC TGC GTC TGT TTG TGT AGT GA 3' | 22 |
| R4 | BRLF1 | 106, 162–106, 201 | 5' AT GGT ATT CTA CTT TAA AAA GGC CGG CTG | 23 |

TABLE I-continued

| Oligonucleotide | Antisense to | EBV genome (B95-8) coordinates (nucleotides; 5'-3') | Sequence | SEQ ID No. |
|---|---|---|---|---|
| | | (splice site in exon 1 to beginning of exon 1) | ACA TGG ATT AC 3' | |
| R5 | BRLF1 | 105, 146–105, 185 AUG in exon 2 into BRLF1 ORF | 5' CT CAG AAA GTC TTC CAA GCC ATC CTT TTT AGG CCT CAT GG 3' | 24 |
| H1 | BHRF1 | 54, 316–54, 355 (intron 1, exon 2) | 5' ACA AAT GTA ATT AAG AGG GAA CTA GAA AAC CAA AAA ATT C 3' | 25 |
| H2 | BHRF1 | 53, 876–53, 915 (splice donor 3, intron 10 | 5' TTT TAA TGG CAA ACA GTT ACC CGA GGT AAG CCG TTC CAG A 3' | 26 |
| H3 | BHRF1 | 48, 425–48, 464 (splice donor, intron 1) | 5' AGA AGG TTG TTG GCA TGT ACC TGC CCA ACC ACA GGT TCA G 3' | 27 |
| H4 | BHRF1 | 47, 980–48, 019 (splice donor 1, intron 1) | 5' AAC TGA AAT TCA CAA ATC ACC TGG CTA AGC CTG TGA CTT A 3' | 28 |
| MS1 | BMLF1 and BSLF2 | 84, 269–84, 308 (AUG Region) | 5' AG TCT CTG AGA AGG AAC CAT CTT GTC TGT CTC TAC GAC GG 3' | 29 |
| M2 | BMLF1 | 84, 207–84, 246 (BMLF1 splice site, exon 1 to intron 1) | 5' CT GGC CGG TGT AGC TTC TTA CCT GCG GGA TCC TCG TTG GA 3' | 30 |
| M3 | BMLF1 | 84, 103–84, 142 (BMLF1 splice site, exon 2 to intron 1) | 5' AG TTC CAG AAT GTG GCT CTC TGC AGA GGG GAG ACA AAA GG 3' | 31 |
| L1 | BLLF1 (gp 350) | 92, 132–92, 171 (AUG Region) | 5' AC ACA AGC AAG GCT GCC TCC ATT GTC TCG GCA CCG ATT TC 3' | 32 |
| NZ1 | BZLF2 (gp 42) | 102, 097–102, 136 (AUG Region) | 5' AC CTG CTT AAA TGA AAC CAT GGC AAC CAC TTC AAA GAG AG 3' | 33 |
| N1 | BNLF1 (LMP-1) | 169, 455–169, 494 (AUG Region) | 5' C TCT CAA GGT CGT GTT CCA TCC TCA GGG CAG TGT GTC AGG 3' | 34 |
| N2 | BNLF1 (LMP-1) | 169, 361–109, 400 (identified by RNAse H assay) | 5' A AAC AGT AGC GCC AAG AGG AGG AGA AGG AGA GCA AGG CCT 3' | 35 |
| N3 | BNLF1 (LMP-1) | 169, 310–169, 349 (identified by RNAse H assay) | 5' G AGG ACA AGG AGG GCT CCT CCA GTC CAG TCA CTC ATA ACG 3' | 36 |
| N4 | BNLF1 (LMP-1) | 169, 187–169, 226 (splice site exon 1 to intron 1) | 5' G CAA AGG GTG TAA TAC TTA CTC ATC AGT AGG AGT ATA CAA 3' | 37 |
| N5 | BNLF1 (LMP-1) | 169 109–169, 148 (splice site intron 1 to exon 2) | 5' A GCG ATG AGC AGG AGG GTG ACT GGG GAA AGA GGA GAA AGT 3' | 38 |
| N6 | BNLF-1 (LMP-1) | 169, 035–169, 074 (splice site exon 2 to intron 2) | 5' ATC TTA CCA AGT AAG CAC CCG AAG ATG AAC AGC ACA ATT C 3' | 39 |
| N7 | BNLF1 (LMP-1) | 168, 934–168, 985 (RNAse H; splice site intron 2 to exon 3) | 5' CAT CTC CAA TAA GTA GAT CCA GAT ACC TAA GAC TGC GTT GAA AAA AGA TGT T 3' | 40 |
| Y1 | BYRF1 (EBNA-2) | 48, 420–48, 381 (coding exon) | 5' AA CTT TAC ACC ACG TCA CAC GCC AGT GCT GGG TTA CTG CG 3' | 41 |
| Y2 | BYRF1 (EBNA-2) | 48, 553–48, 514 (AUG Region) | 5' AT TAG ATG ATA TGT TTG TCC CCC ATG TAA CGC AAG ATA GA 3' | 42 |
| TP1 | Terminal Protein (LMP-2) gene | 78–39 (exon 2 to intron 1, and AUG) | 5' GG CAG GCA TAC TGG ATT CAT ACT AAG AAA GAG AAC GGG CA 3' | 43 |
| TP2 | Terminal protein (LMP-2) gene | 292–253 (exon 2 to intron 2) | 5' AA TGG TGC GTG TGT ACT CAC AAG TGA CAA CCG CAG TAA GC 3' | 44 |
| TP3 | Terminal Protein (LMP-2) gene | 380–341 (intron 2 to exon 3) | 5' AT GTT AGG CAA ATT GCA AAG ACT GAG GAG AAA AGC AGA GG 3' | 45 |
| TP4 | Terminal Protein (LMP-2) gene | 478–439 (exon 3 to intron 3) | 5' CA TAA CAG AGG CAC ACT AAC CGT AAA TGC CTT GTA GTC CG 3' | 46 |
| TP5 | Terminal Protein (LMP-2) gene | 560–521 (exon 3 to intron 4) | 5' GG AGC ACA AGC ATC ACC AGA ACT GAA ATA AAA GTA AAG TT 3' | 47 |

TABLE I-continued

| Oligonucleotide | Antisense to | EBV genome (B95-8) coordinates (nucleotides; 5'-3') | Sequence | SEQ ID No. |
|---|---|---|---|---|
| TP6 | Terminal Protein (LMP-2) gene | 808–769 (intron 4 to exon 4) | 5' AT GTC ACA CGT GTG GCT TAC CTG CTG CCA ATG TTA AAA GG 3' | 48 |
| TP7 | Terminal Protein (LMP-2) gene | 890–851 (intron 4 to exon 5) | 5' TG ACG CTA GCA GTG CCA GAG CTA TAA TCA GAG ATG GCA TG 3' | 49 |
| TP8 | Terminal Protein (LMP-2) gene | 970–931 (exon 5 to intron 5) | 5' AA AGG AAG GAA AAA CTT ACC AAG TGT CCA TAG GAG CAT GA 3' | 50 |
| TP9 | Terminal Protein (LMP-2) gene | 1045–1006 (intron 5 to exon 6) | 5' AG AGC AAA TCA GGA GAA CCA CTG TAA AAG AGA TGC CAA GT 3' | 51 |
| TP10 | Terminal Protein (LMP-2) gene | 1215–1176 (exon 6 to intron 6) | 5' GT AAC AAA TAG ATA CTC ACT GGG TAT AAA TTC AGT GCT GC 3' | 52 |
| TP11 | Terminal Protein (LMP-2) gene | 1300–1261 (inton 6 to exon 7) | 5' GT AAT AAC ATG CAG AAC AAA TCT AAG GAA CAA AGC GTA AA 3' | 53 |
| TP12 | Terminal Protein (LMP-2) gene | 1515–1476 (exon 7 to intron 7) | 5' CC TGT TGG TGT CAC ACT TAC CAA TGA GGA AAA TCA GGA AT 3' | 54 |
| TP13 | Terminal Protein (LMP-2) gene | 1594–1555 (intron 7 to exon 8) | 5' TG ACC CCA AAG AGG GCA AAG CCT ACA AAA GCC AAA CCC AT 3' | 55 |
| TP14 | Terminal Protein (LMP-2) gene | 1702–1663 (exon 8 to intron 8) | 5' TA AAA TTT AAT AAT ACT TAC CTT TAT ACA GTG TTG CGA TA 3' | 56 |
| TP15 | Terminal Protein (LMP-2) gene | 5428–5389 (exon 9 to intron 8) | 5' GCA GGC GAT CTG GTG GGC ATT CTG CAA AAC ATA TGG CAT C 3' | 57 |
| TP16 | Terminal Protein (LMP-2) gene | 166,582–166,543 (AUG Region) | 5' GCA CCA TTT CTA GGG ACC CCA TAG CTG CAG CAG CGA CTG C 3' | 58 |
| TP17 | Terminal Protein (LMP-2) gene | 166,936–166,897 (exon 1) | 5' CAG ATA GAT GGC ACT CTT ACC TTC CTC TGC CCG CTT CTT C 3' | 59 |
| TP18 | Terminal Protein (LMP-2) gene | 78–57; 169,906–169,888 (AUG to spliced exon 1) | 5' GGC AGG CAT ACT GGA TTC ATA CTG AAC CCC CCT AAA GCA C 3' | 60 |
| TP19 | Terminal Protein (LMP-2) gene | 169,926–169,887 | 5' ACC CCA CAG CCT TGC CTC ACC TGA ACC CCC CTA AAG CAC G 3' | 61 |
| V25 | Reverse Sequence of Z1 | | 5' GA AAC GAC TTC TAC TAC CTG GGT TT 3' | 62 |
| S25 | Sense Sequence of Z1 | | 5' CT TTG CTG AAG ATG ATG GAC CCA AA 3' | 63 |

What is claimed is:

1. An antisense oligonucleotide complementary to a portion of the Epstein-Barr Virus (EBV) BZLF1 gene, the oligonucleotide comprising an 8 nucleotide core region consisting of nucleotides 1–8 of SEQ. ID. NO: 5, nucleotides 6–13 of SEQ. ID. NO: 7, nucleotides 7–14 of SEQ. ID. NO: 9, nucleotides 7–14 of SEQ. ID. NO: 11, nucleotides 7–14 of SEQ. ID. NO: 13, nucleotides 7–14 of SEQ. ID. NO: 14, nucleotides 7–14 of SEQ. ID. NO: 16, nucleotides 7–14 of SEQ. ID. NO: 17, or nucleotides 7–14 of SEQ. ID. NO: 18; or comprising a counterpart core region complementary to a portion of a BZLF1 gene from a different strain of Epstein-Barr Virus (EBV), wherein the oligonucleotide inhibits Epstein Barr Virus (EBV) gene expression.

2. An oligonucleotide of claim 1, wherein said oligonucleotide is Z5 (SEQ ID NO:5).

3. An oligonucleotide of claim 1, wherein said oliganucleotide is Z6 (SEQ ID NO:6).

4. An oligonucleotide of claim 1, wherein said oligonucleotide is Z7 (SEQ ID NO:7).

5. An oligonucleotide of claim 1, wherein said oligonucleotide is Z7-40 (SEQ ID NO:8).

6. An oligonucleotide of claim 1, wherein said oligonucleotide is Z8 (SEQ ID NO:9).

7. An oligonucleotide of claim 1, wherein said oligonucleotide is Z8-40 (SEQ ID NO:10).

8. An oligonucleotide of claim 1, wherein said oligonucleotide is Z9 (SEQ ID NO:11).

9. An oligonucleotide of claim 1, wherein said oligonucleotide is Z9-40 (SEQ ID NO: 12).

10. An oligonucleotide of claim 1, wherein said oligonucleotide is Z10 (SEQ ID NO: 13).

11. An oligonucleotide of claim 1, wherein said oligonucleotide is Z11 (SEQ ID NO:14).

12. An oligonucleotide of claim 1, wherein said oligonucleotide is Z11-40 (SEQ ID NO:15).

13. An oligonucleotide of claim 1, wherein said oligonucleotide is Z12 (SEQ ID NO:16).

14. An oligonucleotide of claim 1, wherein said oligonucleotide is Z13 (SEQ ID NO:17).

15. An oligonucleotide of claim 1, wherein said oligonucleotide is Z14 (SEQ ID NO:18).

16. An oligonucleotide of claim 1, wherein said oligonucleotide is modified to achieve greater stability.

17. An expression vector comprising a first nucleotide sequence that is transcribed within a cell to generate a second nucleotide sequence comprising an oligonucleotide or claim 1, wherein said oligonucleotide is an oligoribonucleotide.

18. An antisense oligonucleotide complementary to a portion of the Epstein-Barr Virus (EBV) BRLF1 gene, the oligonucleotide comprising an 8 nucleotide core region consisting of nucleotides 17–24 of SEQ. ID. NO: 19, or comprising a counterpart core region complementary to a portion of a BRLF1 gene from a different strain of Epstein-Barr Virus (EBV), wherein the oligonucleotide inhibits Epstein-Barr Virus (EBV) gene expression.

19. An oligonucleotide of claim 18, wherein the oligonucleotide is R1 (SEQ ID NO:19).

20. An oligonucleotide of claim 18, wherein said oligonucleotide is modified to achieve greater stability.

21. An expression vector comprising a first nucleotide sequence that is transcribed within a cell to generate a second nucleotide sequence comprising an oligonucleotide of claim 18, wherein said oligonucleotide is an oligoribonucleotide.

* * * * *